(12) United States Patent
Jenkins et al.

(10) Patent No.: US 11,317,912 B2
(45) Date of Patent: May 3, 2022

(54) SURGICAL STAPLER WITH ROTATABLE DISTAL TIP

(71) Applicant: Ethicon LLC, Guaynabo, PR (US)

(72) Inventors: Scott A. Jenkins, Mason, OH (US); Jeffery D. Bruns, Cincinnati, OH (US); Robert J. Simms, Liberty Township, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/729,557

(22) Filed: Dec. 30, 2019

(65) Prior Publication Data

US 2020/0237369 A1 Jul. 30, 2020

Related U.S. Application Data

(60) Provisional application No. 62/840,602, filed on Apr. 30, 2019, provisional application No. 62/798,651, filed on Jan. 30, 2019.

(51) Int. Cl.
*A61B 17/072* (2006.01)
*A61B 17/068* (2006.01)

(52) U.S. Cl.
CPC ........ *A61B 17/072* (2013.01); *A61B 17/0684* (2013.01); *A61B 2017/07264* (2013.01);
(Continued)

(58) Field of Classification Search
CPC .............. A61B 17/072; A61B 17/0684; A61B 17/07207; A61B 2017/07264;
(Continued)

(56) References Cited

U.S. PATENT DOCUMENTS 4,805,823 A 2/1989 Rothfuss
5,415,334 A 5/1995 Williamson, IV et al.
(Continued)

FOREIGN PATENT DOCUMENTS

EP 0537453 A1 * 4/1993 ....... A61B 17/07207
EP 2599452 A1 6/2013
(Continued)

OTHER PUBLICATIONS

International Search Report and Written Opinion dated Apr. 8, 2020 for International Application No. PCT/IB2020/050700, 12 pages.
(Continued)

*Primary Examiner* — Stephen F. Gerrity
*Assistant Examiner* — Linda J Hodge
(74) *Attorney, Agent, or Firm* — Frost Brown Todd LLC

(57) ABSTRACT

A surgical stapler that includes a body, a shaft extending from the body, and an end effector in communication with the shaft. The end effector is operable to compress, staple, and cut tissue. The end effector includes a first jaw; a second jaw opposed from the first jaw, and a tip member. The first and second jaws are operable to transition from an open state to a closed state to clamp tissue therebetween. The tip member is coupled with a distal end of the first jaw. The tip member is selectively rotatable along a rotation axis to toggle between a first discrete position and a second discrete position. The tip member in the first discrete position is configured to assume a first orientation relative to the second jaw, and the tip member in the second discrete position is configured to assume a second orientation relative to the second jaw.

20 Claims, 26 Drawing Sheets

(52) U.S. Cl.
CPC ............... *A61B 2017/07271* (2013.01); *A61B 2017/07285* (2013.01)

(58) Field of Classification Search
CPC ........... A61B 2017/07271; A61B 2017/07285; A61B 2017/07257; A61B 2090/08021; A61B 17/22031; A61B 17/28; A61B 17/29; A61B 2017/1125; A61B 2017/2926
USPC ........................................... 227/175.1, 181.1
See application file for complete search history.

(56) References Cited

U.S. PATENT DOCUMENTS

| | | |
|---|---|---|
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,814,055 A | 9/1998 | Knodel et al. |
| 6,978,921 B2 | 12/2005 | Shelton, IV et al. |
| 7,000,818 B2 | 2/2006 | Shelton, IV et al. |
| 7,143,923 B2 | 12/2006 | Shelton, IV et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,644,848 B2 | 1/2010 | Swayze et al. |
| 7,682,368 B1 | 3/2010 | Bombard et al. |
| 7,721,930 B2 | 5/2010 | McKenna et al. |
| 7,866,523 B1 | 1/2011 | White et al. |
| 8,210,411 B2 | 7/2012 | Yates et al. |
| 8,403,196 B2 | 3/2013 | Beardsley et al. |
| 8,408,439 B2 | 4/2013 | Huang et al. |
| 8,453,914 B2 | 6/2013 | Laurent et al. |
| 9,186,142 B2 | 11/2015 | Fanelli et al. |
| 9,517,065 B2 | 12/2016 | Simms et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,913,642 B2 | 3/2018 | Leimbach et al. |
| 9,936,952 B2 | 4/2018 | Demmy |
| 10,092,292 B2 | 10/2018 | Boudreaux et al. |
| D833,010 S | 11/2018 | Harris et al. |
| D836,198 S | 12/2018 | Harris et al. |
| D836,199 S | 12/2018 | Schowalter et al. |
| 10,182,813 B2 | 1/2019 | Leimbach et al. |
| 10,786,252 B2 | 9/2020 | Harris et al. |
| 2010/0094315 A1 | 4/2010 | Beardsley et al. |
| 2011/0106150 A1 | 5/2011 | White et al. |
| 2012/0143218 A1 | 6/2012 | Beardsley et al. |
| 2013/0334280 A1 | 12/2013 | Krehel et al. |
| 2014/0166723 A1 | 6/2014 | Beardsley et al. |
| 2018/0168651 A1* | 6/2018 | Shelton, IV ....... A61B 17/0682 |
| 2018/0235610 A1 | 8/2018 | Harris et al. |
| 2018/0235611 A1 | 8/2018 | Harris et al. |
| 2018/0235619 A1 | 8/2018 | Harris et al. |
| 2019/0000481 A1 | 1/2019 | Harris et al. |
| 2019/0015100 A1 | 1/2019 | Yigit et al. |
| 2020/0015812 A1 | 1/2020 | Harris et al. |
| 2020/0015813 A1 | 1/2020 | Harris et al. |
| 2020/0015814 A1 | 1/2020 | Harris et al. |
| 2020/0015815 A1 | 1/2020 | Harris et al. |
| 2020/0015817 A1 | 1/2020 | Harris et al. |
| 2020/0205825 A1 | 7/2020 | Vendely et al. |
| 2020/0237368 A1 | 7/2020 | Bruns et al. |
| 2020/0237370 A1 | 7/2020 | Fanelli et al. |

FOREIGN PATENT DOCUMENTS

| | | | |
|---|---|---|---|
| EP | 2674111 A2 | 12/2013 | |
| EP | 2777523 A1 * | 9/2014 | ....... A61B 17/07207 |
| WO | WO 2013/151888 A1 | 10/2013 | |
| WO | WO 2016/094236 A1 | 6/2016 | |

OTHER PUBLICATIONS

International Search Report and Written Opinion dated May 4, 2020 for International Application No. PCT/IB2020/050701, 11 pages.
International Search Report and Written Opinion dated Apr. 21, 2020 for International Application No. PCT/IB2020/050703, 11 pages.
European Search Report and Written Opinion dated Apr. 8, 2020 for Application No. EP 20154700.7, 12 pgs.
European Search Report and Written Opinion dated May 8, 2020 for Application No. EP 20154723.9, 10 pgs.
European Search Report and Written Opinion dated Apr. 21, 2020 for Application No. EP 20154720.5, 10 pgs.

* cited by examiner

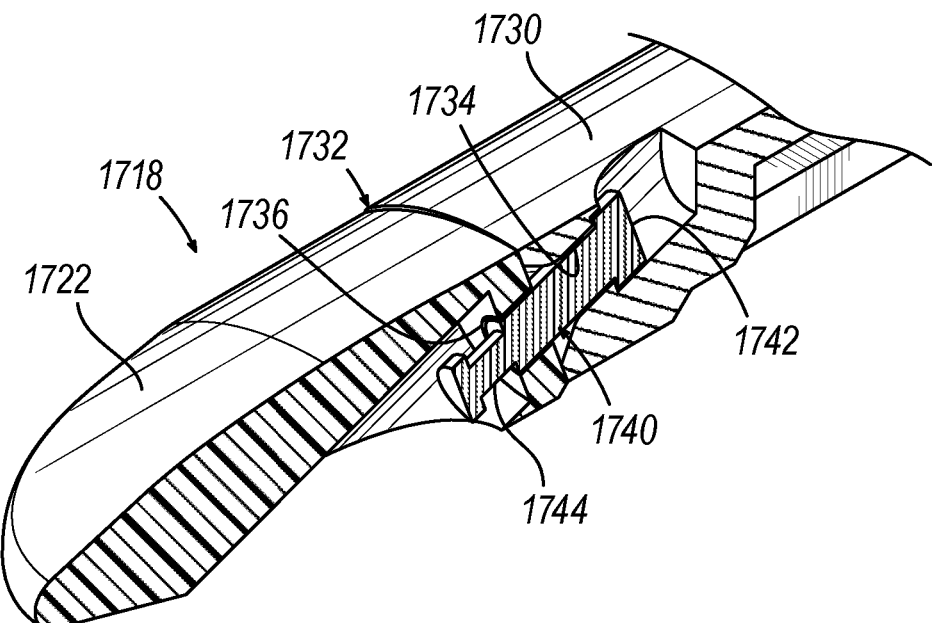
FIG. 29
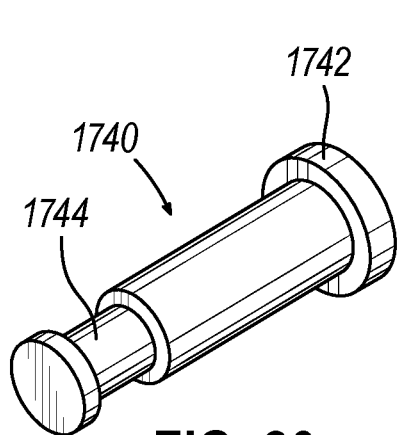 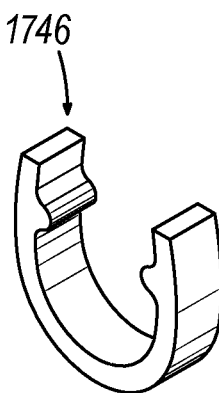 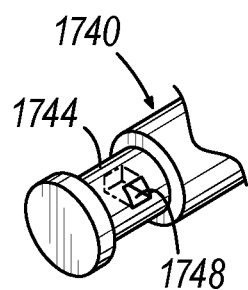
FIG. 30   FIG. 31   FIG. 32

SURGICAL STAPLER WITH ROTATABLE DISTAL TIP

PRIORITY

This application claims priority to U.S. Provisional Patent App. No. 62/798,651, entitled "Surgical Stapler with Adjustable Tip Angulation," filed Jan. 30, 2019 and U.S. Provisional Patent App. No. 62/840,602, entitled "Surgical Stapler with Adjustable Tip Angulation," filed Apr. 30, 2019, the disclosures of which are incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents, U.S. patent Publications, and U.S. patent applications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 29 depicts a perspective of a distal portion of another exemplary anvil having a selectively rotatable distal tip and a tip locking mechanism, showing the distal tip in phantom to reveal internal features;

FIG. 30 depicts a perspective view of an exemplary shaft that permits rotation of the distal tip of the anvil of FIG. 29;

FIG. 31 depicts a perspective view of an exemplary clip configured to secure the shaft of FIG. 30 axially relative to the distal tip and a connection member of FIG. 29; and FIG. 32 depicts an enlarged perspective view of a distal portion of the shaft of FIG. 30, showing an exemplary detent feature of the tip locking mechanism of the anvil.

Figure 1:
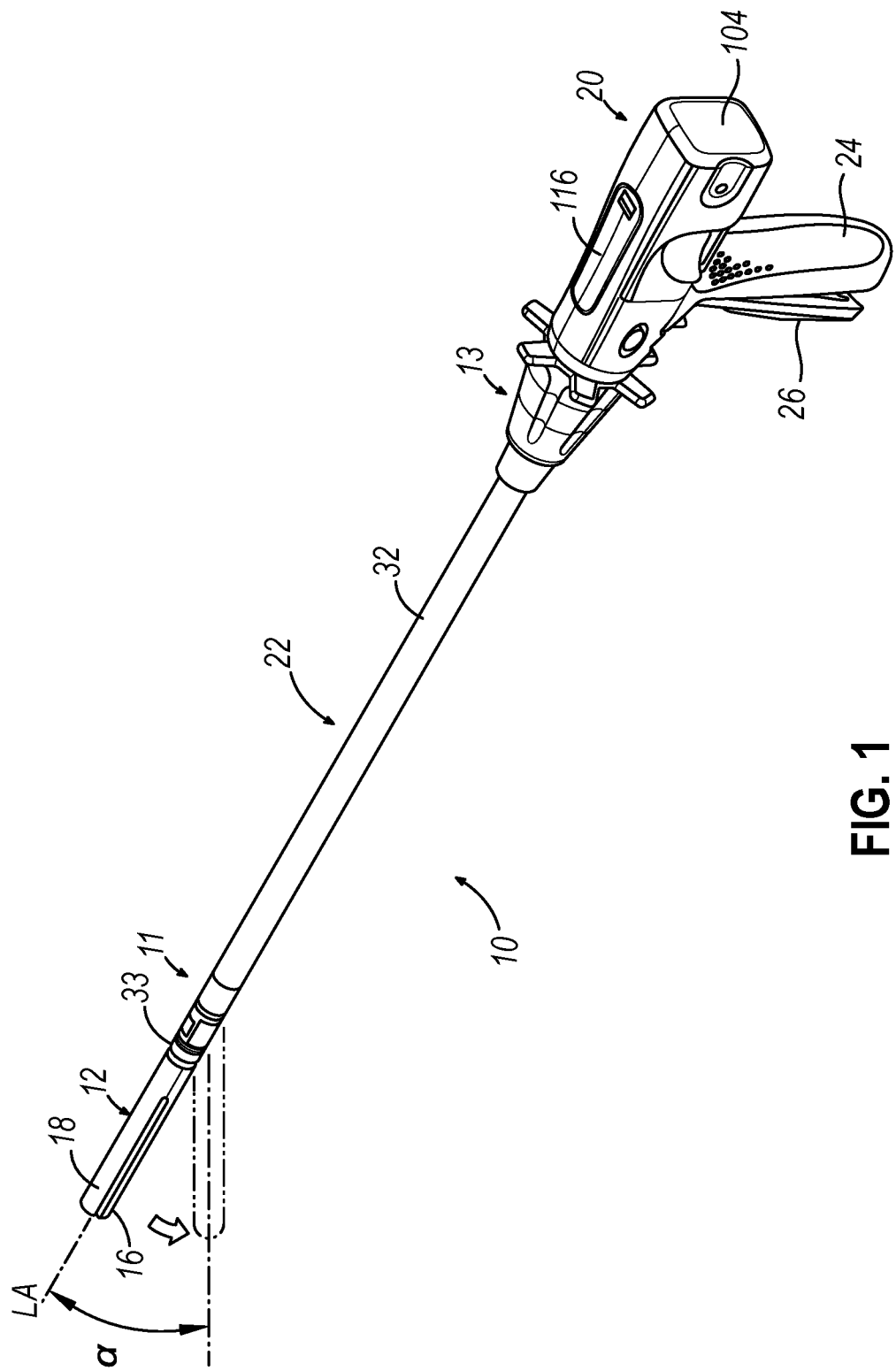
FIG. 1 depicts a perspective view of an exemplary articulating surgical stapling instrument.
Figure 2:
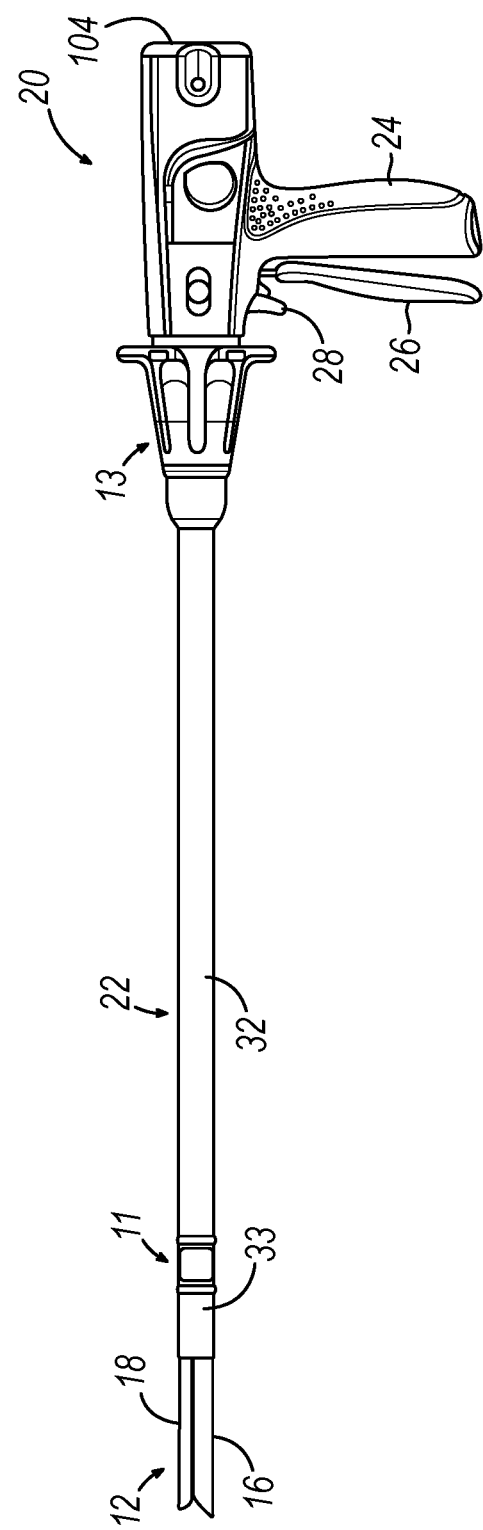
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and an upper jaw in the form of a pivotable anvil (18). In some versions, lower jaw (16) is constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued on Dec. 13, 2016, the disclosure of which is incorporated by reference herein; at least some of the teachings of U.S. Pat. No. 9,839,421, entitled "Jaw Closure Feature for End Effector of Surgical Instrument," issued on Dec. 12, 2017, the disclosure of which is incorporated by reference herein; and/or at least some of the teachings of U.S. Pat. No. 10,092,292, entitled "Staple Forming Features for Surgical Stapling Instrument," issued Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein. Other suitable forms that firing beam (14) may take will be apparent to those of ordinary skill in the art in view of the teachings herein.

Figure 3:
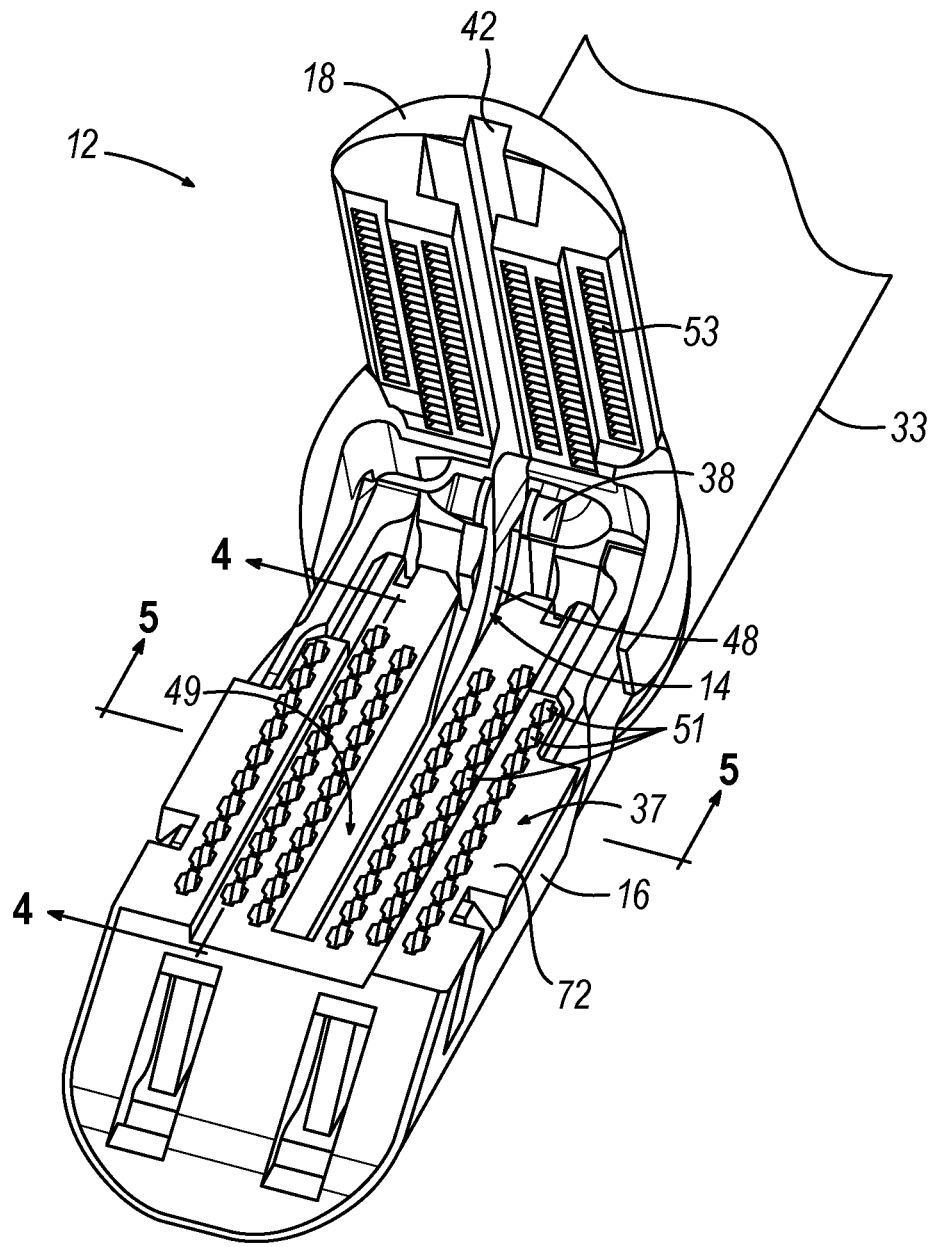
FIG. 3 depicts a perspective view of an opened end effector of the instrument of FIG. 1.
Figure 5:
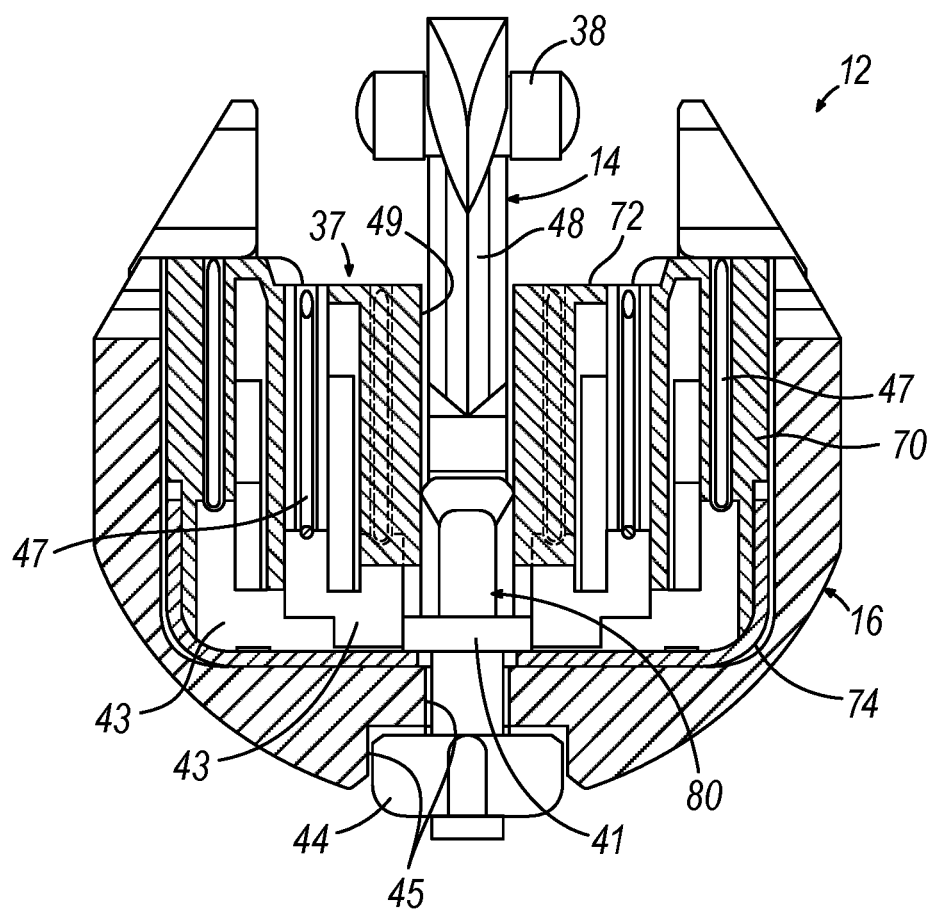
FIG. 5 depicts an end cross-sectional view of the end effector of FIG. 3, taken along line 5-5 of FIG. 3.
Figure 6:
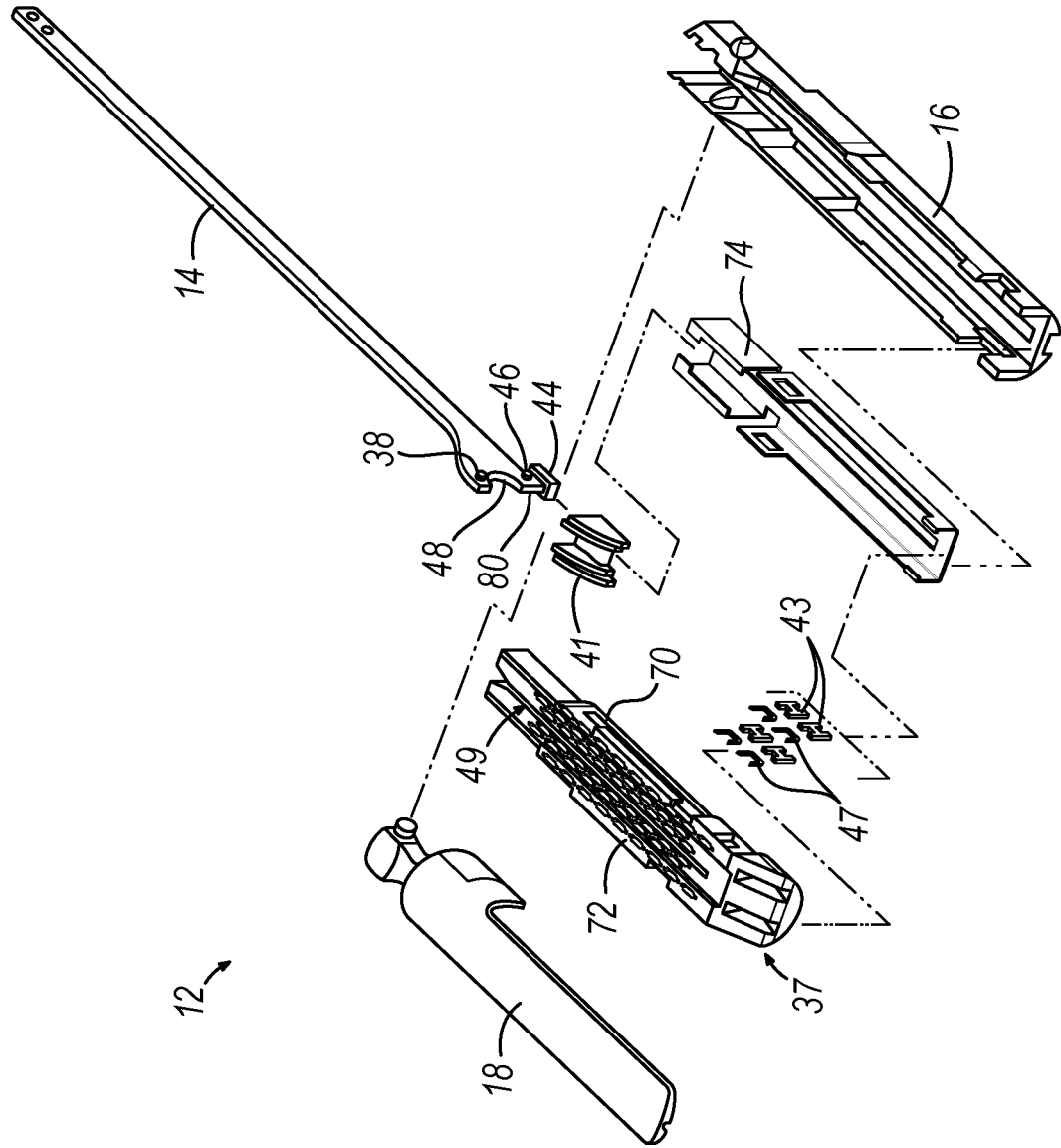
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck

Figure 4A:
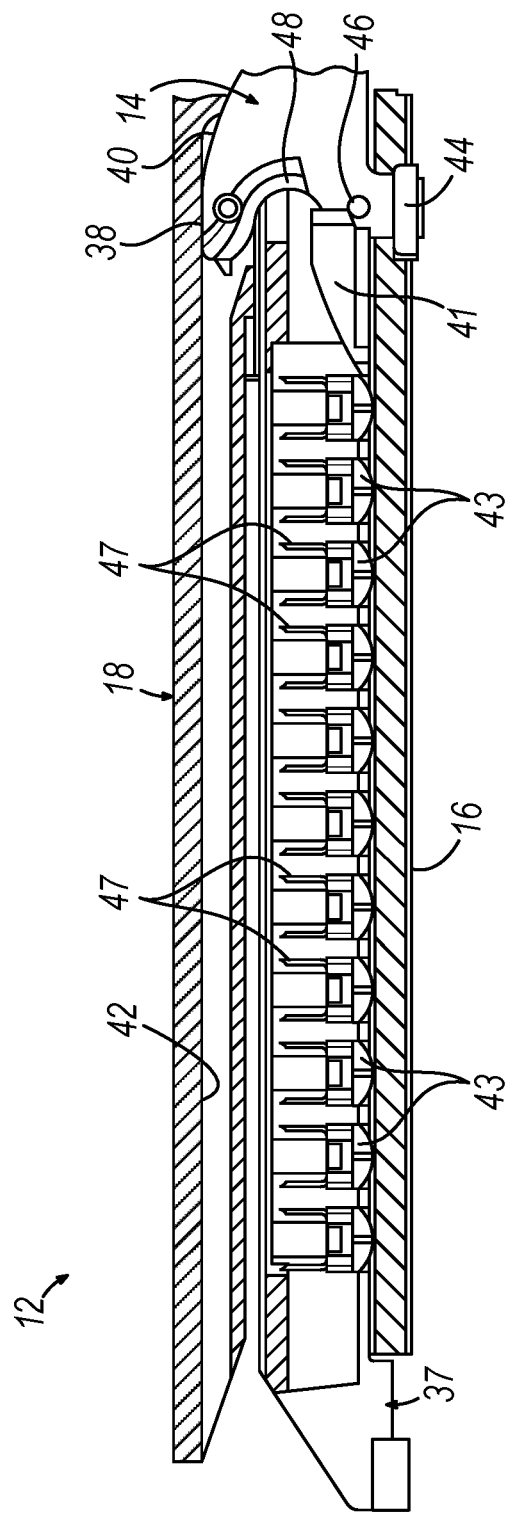
FIG. 4A depicts a side cross-sectional view of the end effector of FIG. 3, taken along line 4-4 of FIG. 3, with the firing beam in a proximal position.
Figure 4B:
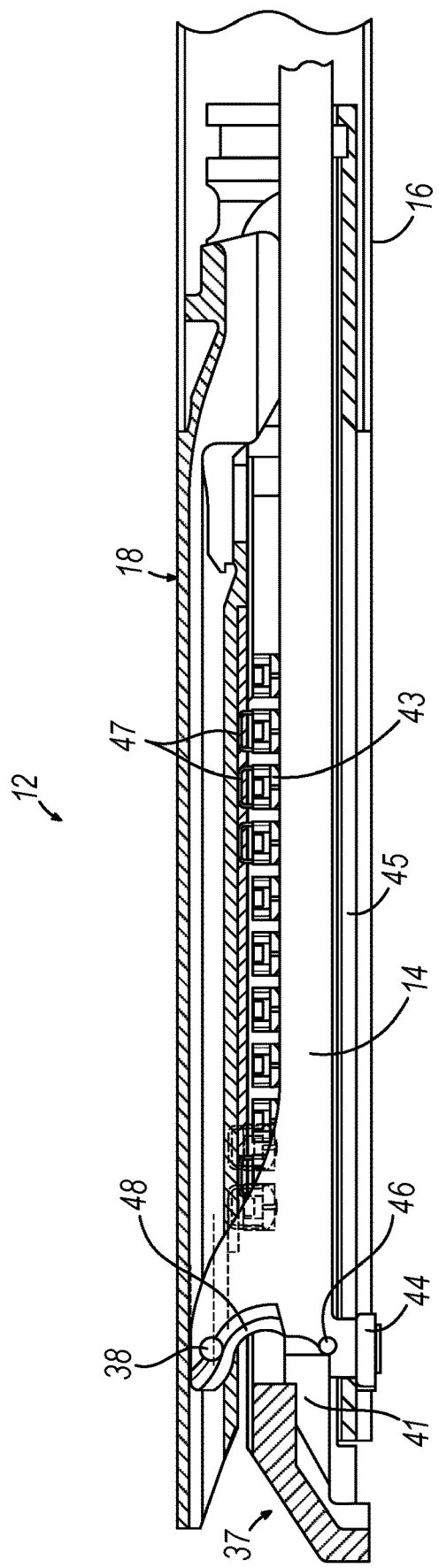
FIG. 4B depicts a side cross-sectional view of the end effector of FIG. 3, taken along line 4-4 of FIG. 3, with the firing beam in a distal position.

(72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein. In addition or in the alternative, staple cartridge (37) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
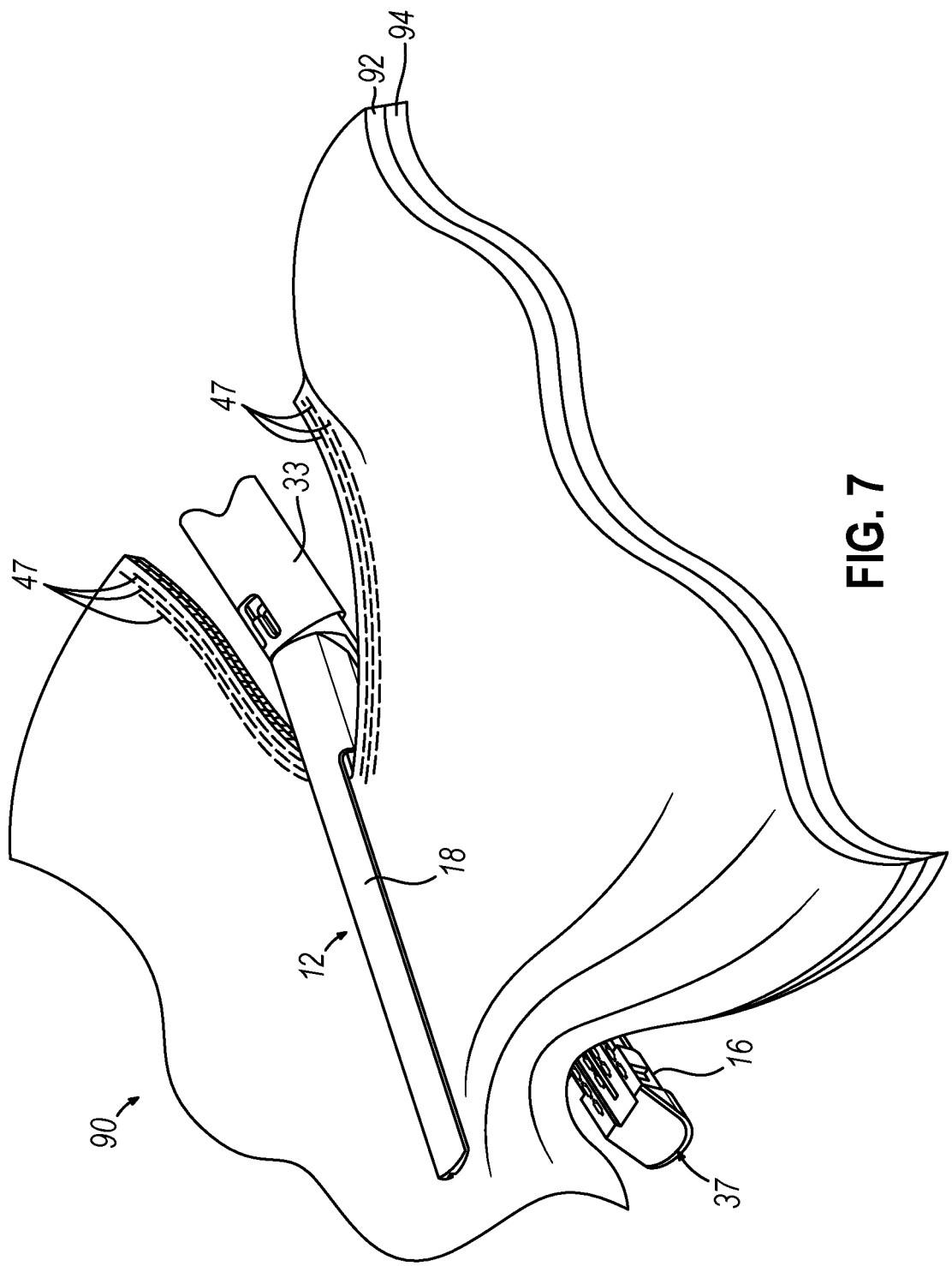
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in U.S. Pat. No. 9,622,746, entitled "Distal Tip Features for End Effector of Surgical Instrument," issued Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pat. No. 8,453,914, the disclosure of which is incorporated by reference herein; and/or in accordance with at least some of the teachings of U.S. Pat. No. 8,453, 914, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in U.S. Pat. No. 9,622,746, entitled "Distal Tip Features for End Effector of Surgical Instrument," issued Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; 8,408,439; and/or 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effector with Visualization, Lead-in, and Gathering Feature

In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
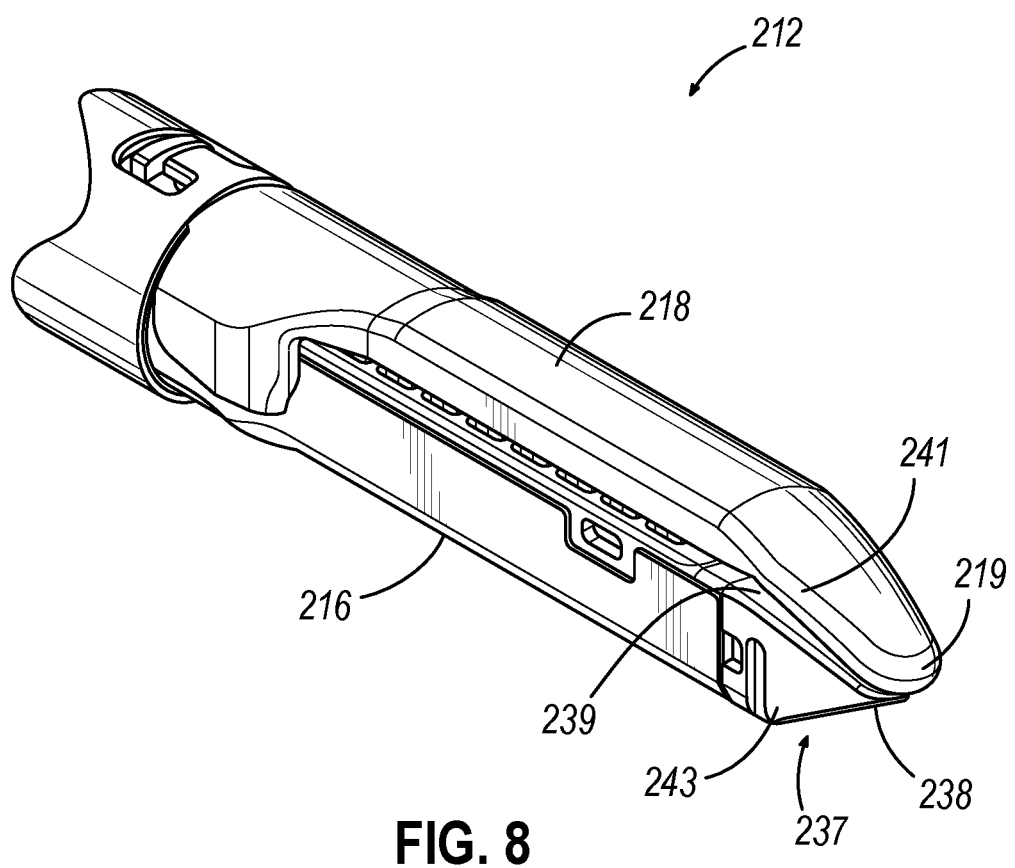
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
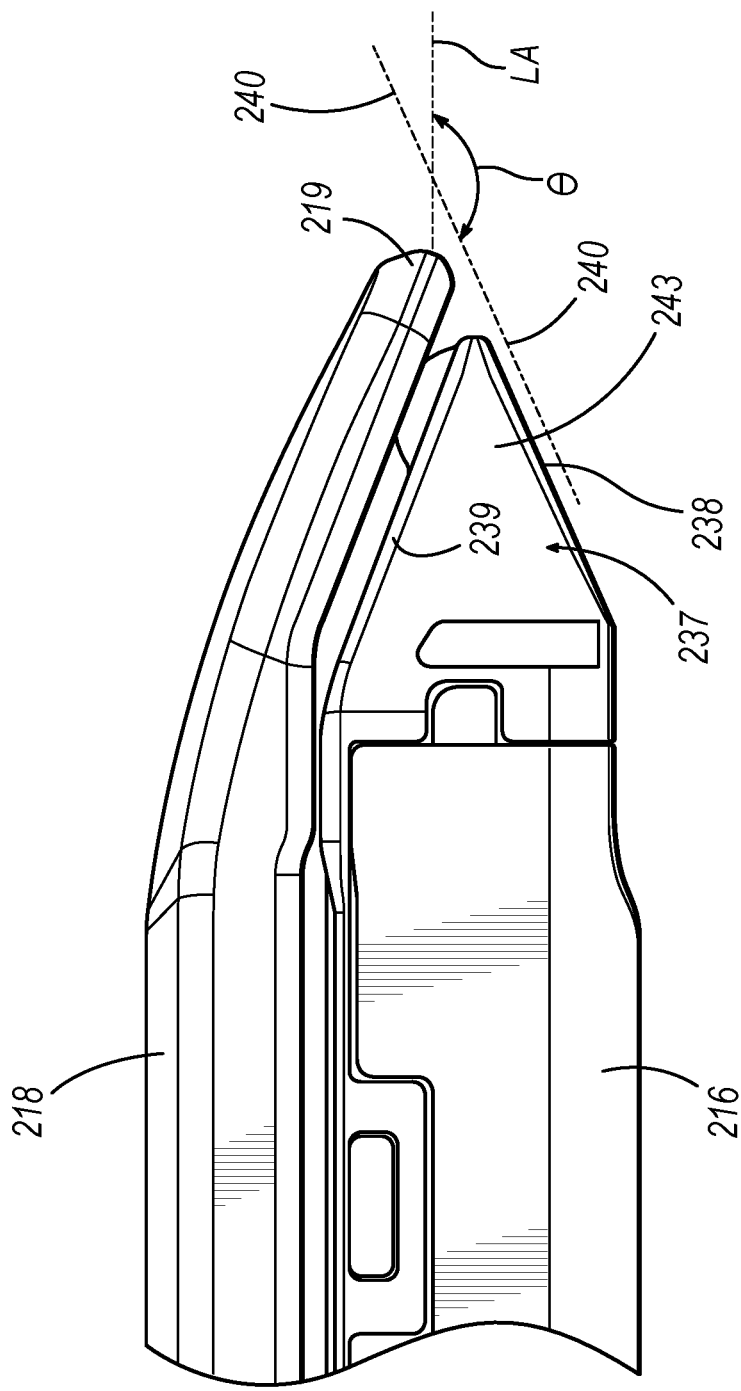
FIG. 9 depicts an enlarged, side view of the end effector of FIG. 8.
Figure 10:
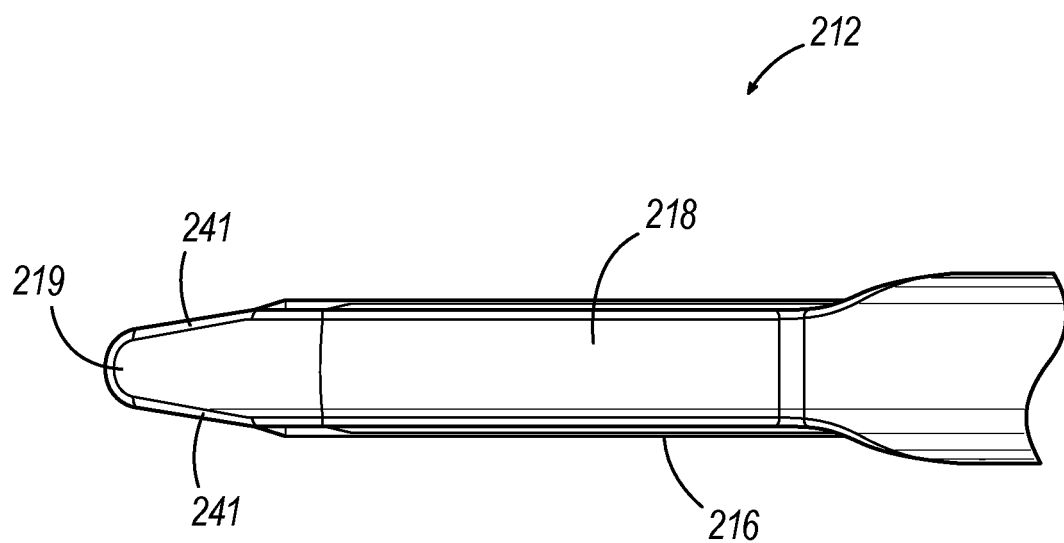
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle (θ).

Viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (212) will be described in greater detail below.

III. End Effectors with Angled Elastically Deformable Anvil Tips

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS.

4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218) may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Figure 11:
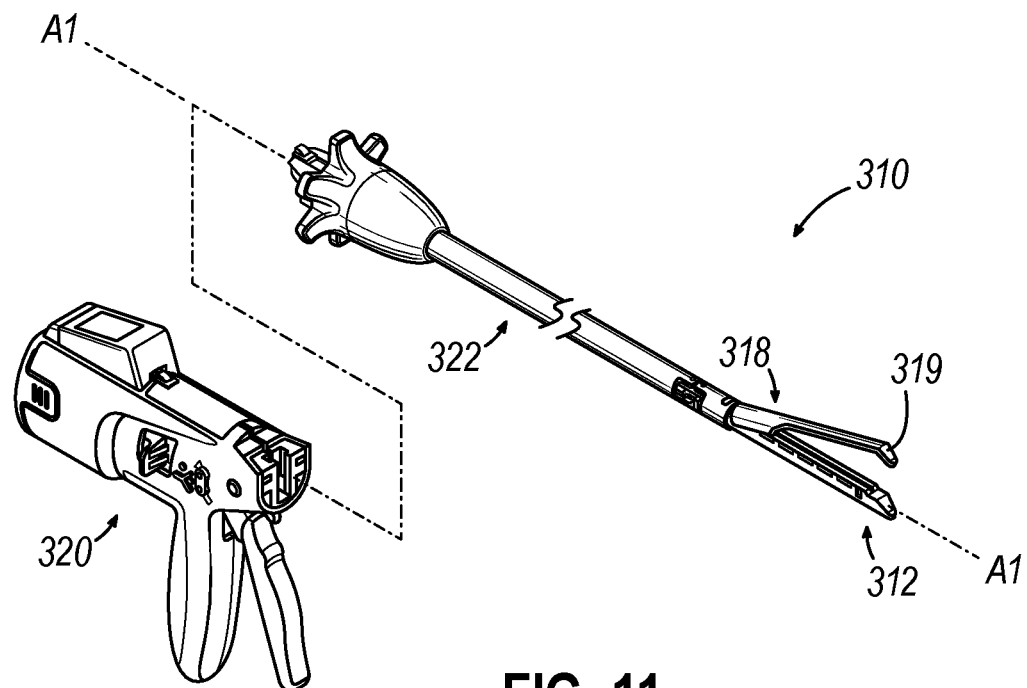
FIG. 11 depicts a perspective view of an exemplary surgical stapling instrument having an end effector with a curved elastically deformable tip section.

FIG. 11 shows another exemplary instrument (310) configured as a surgical stapler. Instrument (310) comprises a handle portion (320) and a shaft (322). Instrument (310) has a modular configuration such that shaft (322) is selectively removable from, and attachable to, handle portion (320). Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) comprises an end effector (312) having an anvil (318) that has an angled distal tip (319). Furthermore, distal tip (319) of anvil (318) is elastically deformable. In this manner, and as shown best in FIGS. 12A and 12B, angled distal tip (319) is operable to elastically deform from a first angled position to a second position. The second position for angled distal tip (319) may be substantially straight in some versions, but may be angled to a degree (e.g., slightly above or slightly below the longitudinal axis (A1)) in other versions. It should be understood that the second position for angled distal tip (319) may be defined by the characteristics (e.g., thickness, density, etc.) of the tissue that is being captured between anvil (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

Figure 12A:
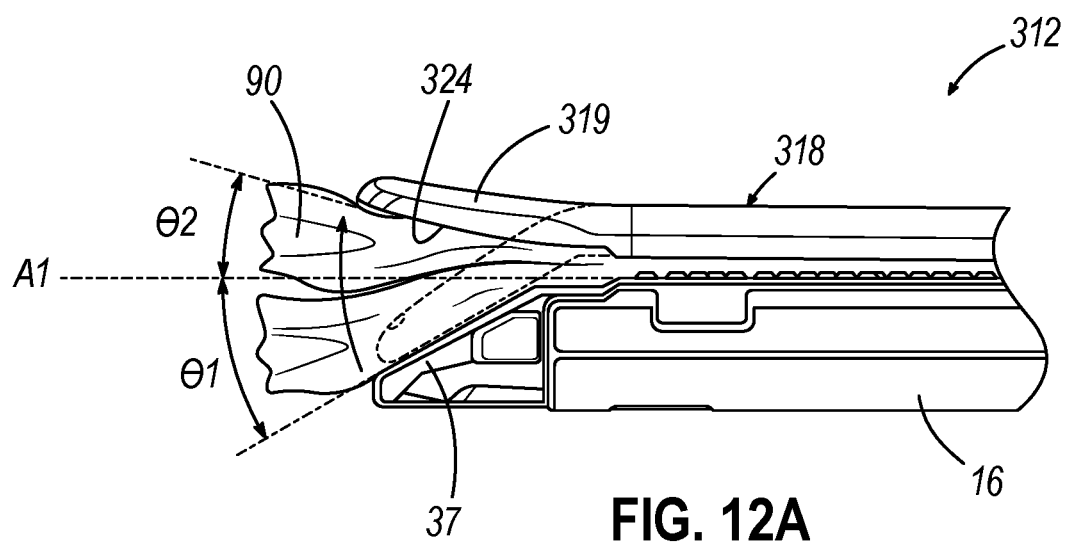
FIG. 12A depicts an enlarged side view of a distal portion of the end effector of FIG. 11.

FIG. 12A shows an enlarged side view of the distal end of end effector (312). End effector (312) comprises anvil (318) and lower jaw (16) that accepts cartridge (37) as described above with respect to instrument (10). Anvil (318) pivotably rotates toward lower jaw (16) in the same manner as anvil (18) as described above with respect to instrument (10). In this configuration, end effector (312) is similar to end effector (12), however, anvil (318) comprises angled distal tip (319) that is elastically deformable. As shown in FIG. 12A, tip (319) is imparted with a bias to an angled position that is shown in FIG. 11 and in phantom in FIG. 12A. Tip (319) assumes this angled position when end effector (312) is not clamping tissue and is open, as shown in FIG. 11; or closed without clamping tissue, as shown in phantom in FIG. 12A. In instances when end effector (312) is in this angled state or position, end effector (312) can be considered not loaded or in a non-loaded state or position. Conversely when end effector (312) is clamping tissue, end effector (312) can be considered loaded or in a loaded state or position.

When closed and not clamping tissue between anvil (318) and lower jaw (16), tip (319) contacts cartridge (37). In this position, an underside surface (324) of tip (319) defines a plane that intersects a longitudinal axis (A1) defined by shaft (322) to form an angle (θ1). When closed and clamping tissue (90) between anvil (318) and lower jaw (16), underside surface (324) of tip (319) contacts cartridge (37). In this position, underside surface (324) of tip (319) defines a plane that intersects longitudinal axis (A1) to form an angle (θ2). In the illustrated example of FIG. 12A, angles (θ1, θ2) are relative to longitudinal axis (A1), and the sum of angles (θ1, θ2) represent the range of motion distal tip (319) undergoes. By way of example only, and not limitation, in some examples angle (θ1) is between about 20 and about 70 degrees, or more particularly between about 30 degrees and about 50 degrees, in a downward direction from longitudinal axis (A1) toward cartridge (37). By way of example only, and not limitation, in some examples angle (θ2) is between about 0 and about 90 degrees in an upward direction from longitudinal axis (A1) away from cartridge (37). By way of example only, and not limitation, in some examples the range of motion undergone by tip (319) is between about 20 degrees and about 110 degrees. The angles described for angles (θ1, θ2) are exemplary only and not limiting. Other suitable angles will be apparent to those of ordinary skill in the art in view of the teachings herein.

Additionally, in some instances longitudinal axis (A1) represents a zero-degree reference and angles relative thereto may be positive or negative. For instance, where an angle is in a downward direction from longitudinal axis (A1) toward cartridge (37), the angle may be characterized as a negative angle. Similarly, where an angle is in an upward direction from longitudinal axis (A1) away from cartridge (37), the angle may be characterized as a positive angle. When using these conventions, the range of motion of distal tip (319) due to deformation can be understood as the sum of the absolute value of the angle when distal tip (319) is in the position contacting cartridge (37), and the angle when distal tip (319) is in the deformed state when clamping tissue.

Figure 12B:
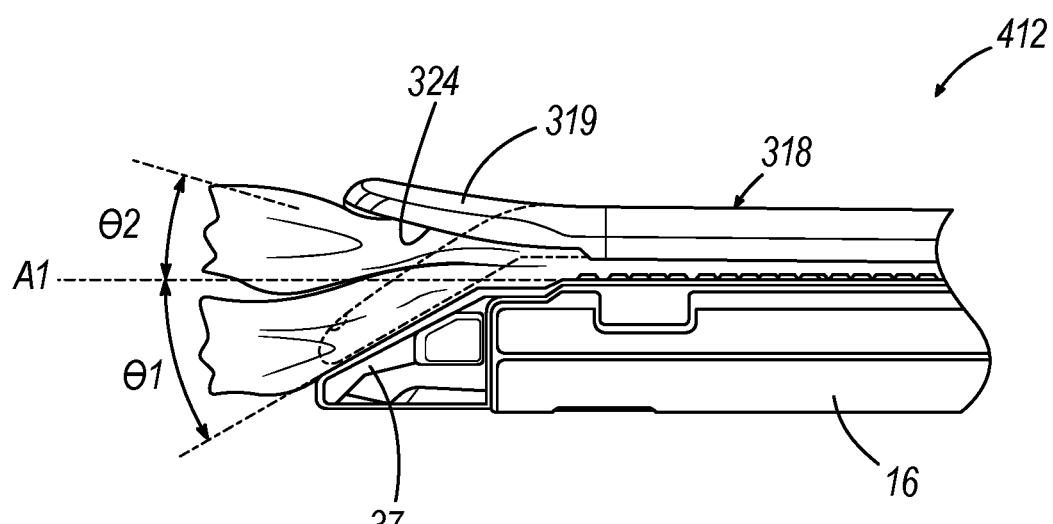
FIG. 12B depicts an enlarged side view of a distal portion of an alternate end effector similar to that of FIG. 11.
Figure 13:
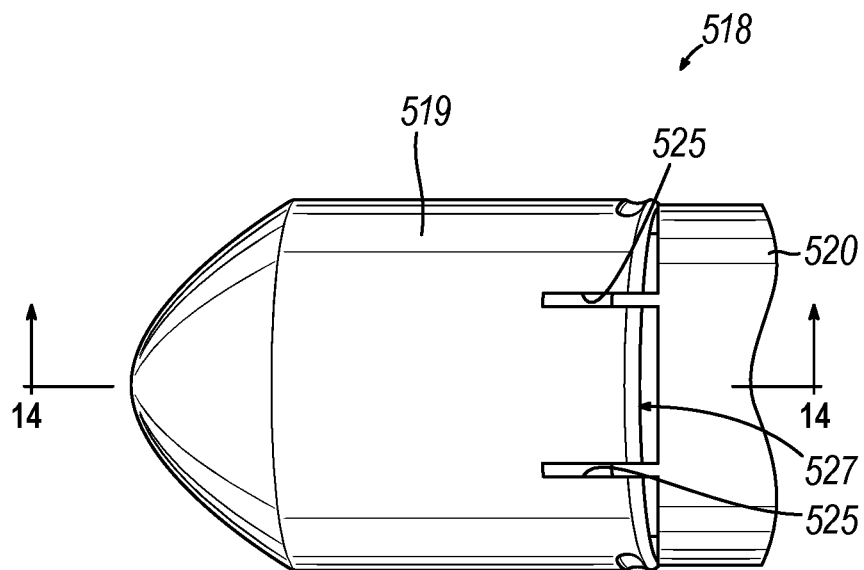
FIG. 13 depicts a partial top view of an alternate anvil of an end effector for use with the surgical instruments described herein.

FIG. 12B shows another side view of an alternate end effector (412) similar to end effector (312) of FIG. 12A. With end effector (312), when anvil (318) is in its angled and non-deformed state (as seen in phantom in the view of FIG. 12A), anvil (318) extends to a point even with or proximal to the distal most end of cartridge (37). When anvil (318) is deformed such that it is deflected upwardly, the end of distal tip (319) extends to a point just distal to the distal most end of cartridge (37). With end effector (412), as shown in FIG. 12B, when anvil (318) is in its angled and non-deformed state (as seen in phantom in the view of FIG. 12B), anvil (318) extends to a point even with or proximal to the distal most end of cartridge (37). When anvil (318) is deformed such that it is deflected upwardly, the end of a distal tip (319) of anvil (318) extends to a point even with or proximal to the distal most end of cartridge (37). In this manner, anvil (318) of end effector (412) remains even with or proximal to the distal most end of cartridge (37) when anvil (318) is in its angled state or deformed state such that anvil (318) does not extend past the distal most end of cartridge (37) whether anvil (318) is in its angled and non-deformed state or in its deformed state. In some instances, this can be achieved by modifying anvil (318) such that distal tip (319) of anvil is shortened in length. In other instances, instruments (10, 310) may be modified to provide for a slight proximal retraction of anvil (318) when clamping. In view of the teachings herein, other ways to modify end effector (412) as it relates to control of anvil (318) position, will be apparent to those of ordinary skill in the art.

IV. Exemplary End Effectors with Discrete Position Pivoting Tips

In some instances, it may be desirable to provide the user with a versatile end effector with a tip that can take on different configurations for differing applications. For instance, it may be desirable or beneficial to a user to use an end effector with an angled (or "bent") tip for the visualization and placement benefits as described above. Furthermore, not only visualization of the distal end of the end effector may be desirable, but also it may be desirable to construct the end effector such that the distal end of the anvil is configured to urge tissue (e.g., a large vessel) proximally into the space between the anvil and the lower jaw as the anvil closes toward the lower jaw. Still in other circumstances, it may be desirable or beneficial to a user to use an end effector with a straight or flared tip so the end effector better accommodates procedures involving marching as also discussed above. Furthermore, it may be desirable or beneficial for a user to be able to toggle a tip of the end effector out of the way when the user is concerned about the pressure on the tissue under the tip in use.

It will be appreciated that the terms "angled" and "bent" as used herein in connection with the various exemplary anvil tips disclosed encompass tip configurations in which the tip defines a flat planar exterior surface that extends angularly in a distal direction from the distal end of the anvil body; and also tip configurations in which the tip defines a curved exterior surface that extends arcuately in a distal direction from the distal end of the anvil body (e.g., where the tip is said to be in a "curved" configuration). In both such types of configurations, a distal end of the anvil tip is vertically offset from a longitudinal axis of the anvil body along an axis that extends transversely to the longitudinal axis and through the corresponding staple cartridge, such that the tip as a whole is "angled" or "bent" relative to the anvil body.

A. Exemplary End Effector Pinned Pivoting Tip with Detents

FIGS. 13-16 depict exemplary anvils (518, 118) usable with the end effectors described herein and others. For instance, anvils (518, 118) can be interchanged or used in place of anvils (18, 218, 318) of respective end effectors (12, 212, 312, 412) described above. It will be appreciated that end effectors (12, 212, 312, 412) incorporating either of anvils (518, 118) may be used with instruments (10, 310) and the other surgical instruments described herein. To this extent, end effectors (12, 212, 312, 412) incorporating either of anvils (518, 118) may be integrally formed with instruments (10, 310) and the other surgical instruments described herein, or in the alternative may be interchangeable end effectors of instruments (10, 310) and the other surgical instruments described herein.

As part of any of end effectors (12, 212, 312, 412), anvils (518, 118) are operable to pivot relative to lower jaws (16, 216). Anvils (518, 118) and lower jaws (16, 216) may clamp tissue (90) similarly to clamping performed by anvil (18) and lower jaw (16) shown in FIG. 7. Anvils (518, 118) and lower jaws (16, 216) may further cut and staple clamped tissue (90) similarly to the cutting and stapling performed by anvil (18) and lower jaw (16) shown in FIG. 7. To accomplish the cutting and stapling, as described above, end effectors (12, 212, 312, 412) incorporating either of anvils (518, 118) further comprises a cartridge (37, 237) containing staples where cartridge (37, 237) is operable to be placed in lower jaw (16, 216).

1. Single Section Pinned Pivoting Tip

Anvil (518) comprises a body (520) and a tip (519) extending distally from body (520). Proximal to tip (519), anvil (518) comprises an extension (502) on body (520). Anvil (518) further comprises a pair of spaced apart detents (504). A portion of detents (504) located on extension (502) are configured as raised portions or protrusions (510) as shown in the illustrated version. The other portion of detents (504) are located on tip (519) and are configured as recesses (523) as will be discussed further below. Anvil (518) also comprises a bore (506) that extends through the sides of body (520) of anvil (518) and bore (506) is configured to receive a pin (508). As will be discussed further below, pin (508) defines an axis of rotation about which tip (519) is rotatable.

Tip (519) comprises a bore (521) that extends through the sides of tip (519) and bore (521) is configured to also receive pin (508). In this manner, tip (519) is operable to rotate about pin (508) and thus rotate relative to a longitudinal axis (A2) of anvil (518). Bores (506, 521) have a circular shape, but in other examples have an elongated shape. In some instances an elongated shape for bores (506, 521) provides for or contributes to tip (519) assuming different discrete positions as discussed further below. As mentioned above, tip (519) comprises a pair of recesses (523) that are configured to be selectively engageable with raised portions or protrusions (510) of detents (504). At a proximal part of tip (519), tip (519) comprises a pair of slots (525) that extend longitudinally and define a resilient portion (527). In the present example, resilient portion (527) comprises recesses (523) along an underside of resilient portion (527).

Figure 14A:
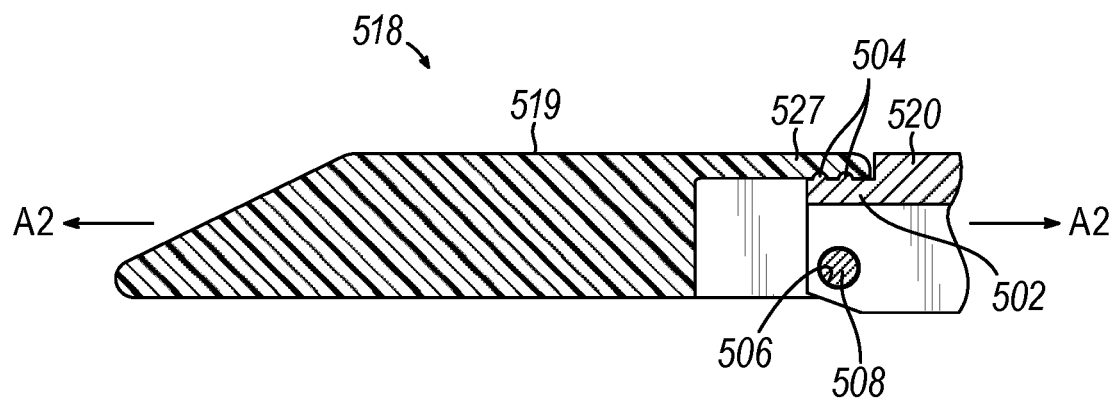
FIG. 14A depicts a cross sectional side view of the anvil of FIG. 13, taken along line 14-14 of FIG. 13, and showing a tip of the anvil in a first position.
Figure 14B:
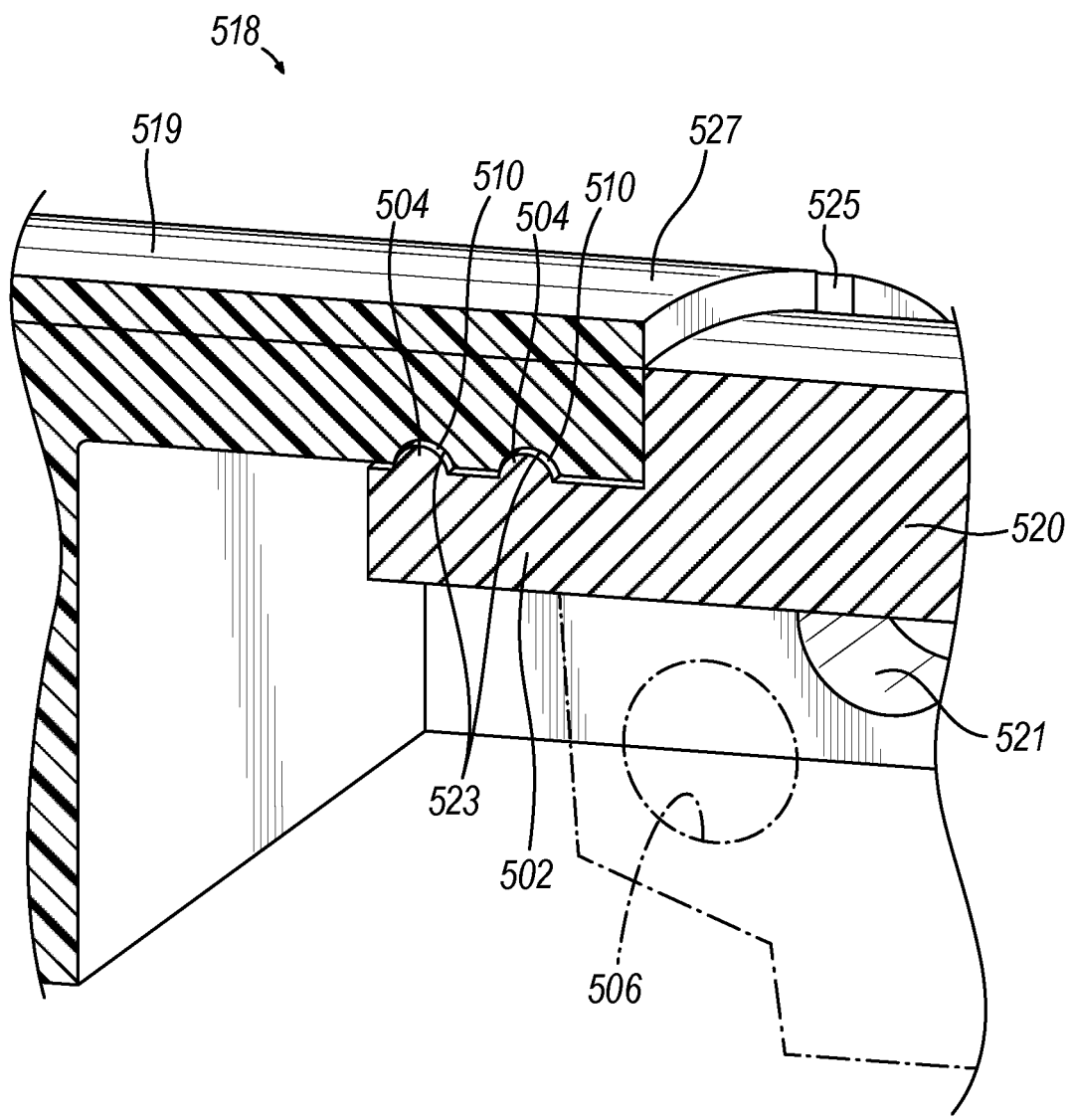
FIG. 14B depicts an enlarged perspective view of the anvil of FIG. 14A, shown with a portion of the anvil in phantom.
Figure 15:
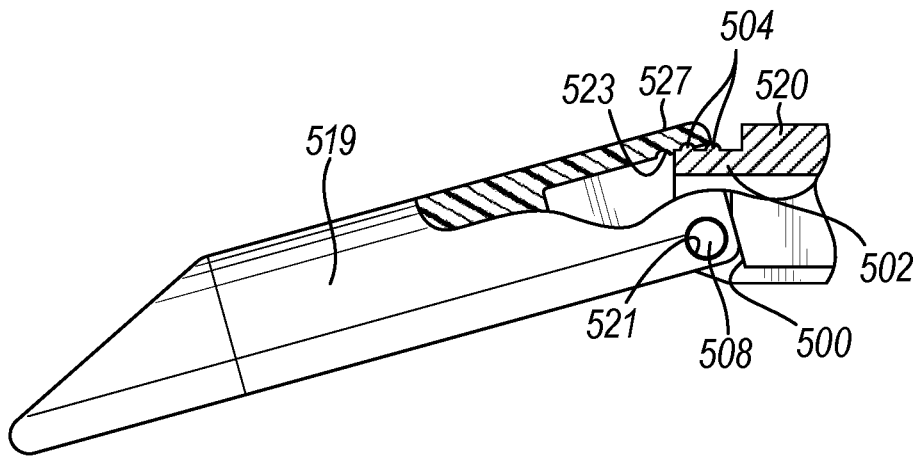
FIG. 15 depicts a side view of the anvil of FIG. 13, showing the tip of the anvil rotated to a second position.

Referring now to FIG. 14A and FIG. 15, anvil (518) is configured with tip (519) that can be moved into discrete positions. Detents (504) provide for selective engagement between raised portions (510) of detents (504) and recesses (523) of detents (504), which allow for tip (519) to move to different discrete positions. FIG. 14A illustrates tip (519) is a first position that has tip (519) in a straight orientation such that a longitudinal axis of tip (519) is generally parallel with or coincides with longitudinal axis (A2) of anvil (518). FIG. 15 illustrates tip (519) in a second position that has tip (519) in An angled orientation such that the longitudinal axis of tip (519) forms an angle with longitudinal axis (A2) of anvil (518) that is less than about 180 degrees.

As described above and illustrated in FIGS. 13-15, slots (525) define resilient portion (527), such that resilient portion (527) acts as a spring to thereby allow tip (519) to change positions by recesses (523) engaging raised portions (510) in different manners. For instance, when in the straight orientation as shown in FIG. 14A, the proximal most recess (523) engages with the proximal most raised portion (510). Similarly, in this straight orientation the distal most recess (523) engages with the distal most raised portion (510). When in the angled orientation as shown in FIG. 15, the proximal most recess (523) engages with the distal most raised portion (510). Furthermore, in this angled orientation the distal most recess (523) is not engaged with either raised portion (510). However, anvil (518) comprises a stop feature (500) that is configured to contact a proximal end of tip (519) and prevent tip (519) from moving to an even further angled position. With the engagement between one or more recesses (523) and one or more raised portions (510) in each of the straight orientations, tip (519) is adjustable or positionable in discrete positions rather than having a continuum of orientations. Thus tip (519) is configured to adopt discrete positions where tip (519) remains in one of the discrete positions until acted upon by a force sufficient to overcome the interference connection established between recesses (523) and raised portions (510) of detents (504).

Referring to FIG. 15, when tip (519) is rotated or pivoted to the angled orientation illustrated, a gap (529) can be present in some versions. An optional sleeve (not shown) can be added to anvil (518) to cover or extend over gap (529) to remove the possibility that gap (529) could present a pinch point for surrounding tissue. In some examples, such a sleeve could extend to reach the end of tip (519) and go as far back as the stapling line of anvil (518), although this would not be required in all versions.

In the one version of anvil (518), anvil (518) is constructed of a single material such as stainless steel, but other materials instead of stainless steel can be used in other versions. Furthermore, in some other versions, anvil (518) can be overcoated with another material to provide for visualization, sliding, or other material properties or attributes as will be apparent to those of ordinary skill in the art in view of the teachings herein.

In other examples of anvil (518), three detents (504) can be used such that three discrete positions for tip (519) can be defined. In such a version with three detents (504), tip (519) can be configured to adopt either a straight orientation, an angled orientation (which may form a curved configuration), or a flared or open orientation where tip (519) is bent upward away from lower jaw (16, 216). Also, in other examples of anvil (518), detents (504) can be located on the sides of tip (519) and body (520) of anvil (518) instead of the top. Still yet, in some other examples, the location of the features of detents (504) can be opposite. For instance, instead of raised portions (510) being located on body (520) of anvil (518), raised portions are located on tip (519). In such an example, instead of slots (525) and resilient portion (527) with recesses (523) being located on tip (519), slots (525) and resilient portion (527) with recesses (523) are located on body (520) of anvil (518). In such an example, these features still cooperate in the same manner as described above to provide for discrete positioning of tip (519). In view of the teachings herein, other ways to configure anvil (518) and detents (504) to achieve multiple discrete positions for tip (519) will be apparent to those of ordinary skill in the art.

2. Multiple Sections Pinned Pivoting Tip

Figure 16:
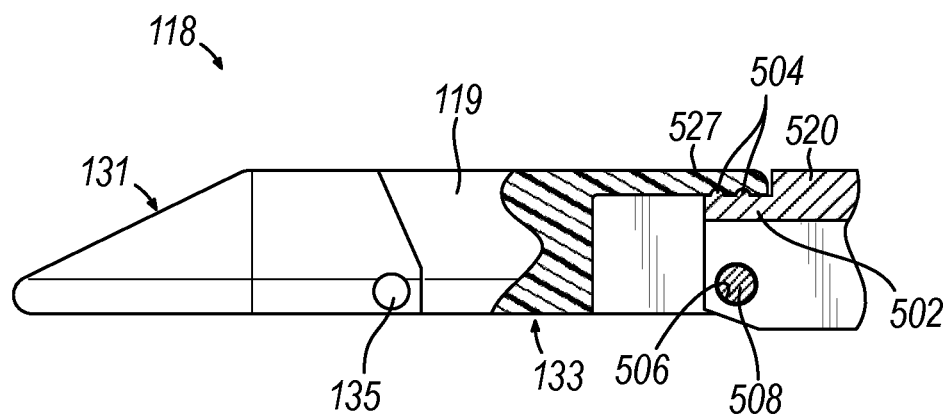
FIG. 16 depicts a cross sectional side view of an alternate anvil of an end effector for use with the surgical instruments described herein, and similar to the anvil of FIG. 14 but having multiple rotatable tip portions.

FIG. 16 illustrates another exemplary anvil (118) usable with the end effectors described herein and others. Anvil (118) is similar to anvil (518) described above except for the differences noted below. Thus, the description above for anvil (518) applies equally to anvil (118).

Anvil (118) comprises a body (520) and a tip (119) extending distally from body (520). The features and functions of anvil (518) apply equally to anvil (118) including the features and functions of tip (519) applying equally to tip (119). However, tip (119) includes additional features and functionality. Specifically, tip (119) comprises a distal portion (131) and a proximal portion (133). Furthermore, tip (119) is configured such that not only is proximal portion (133) rotatable to discrete positions relative to body (520) of anvil (118) as described above with respect to anvil (118), but distal portion (131) is rotatable to discrete positions relative to proximal portion (133) of tip (119).

Moreover, in the illustrated version, the rotatability of distal portion (131) relative to proximal portion (133) occurs in the same manner as the rotatability of proximal portion (133) relative to body (520) of anvil (118). As shown in FIG. 16, a pin (135) extends through and connects distal portion (131) and proximal portion (133). And further pin (135) provides and defines an axis of rotation about which distal portion (131) may rotate. In this manner, tip (119) is comprised of multiple pinned pieces or sections. This configuration allows for a greater angle and also in some versions an overall curvature-like shape to be achieved with otherwise straight but angled sections of tip (119).

As mentioned, the same or similar configuration of detents (504) can be used with distal and proximal portions (131, 133) of tip (119) to achieve the rotation to discrete positions. For example, in one version a first discrete position for distal portion (131) is a straight orientation relative to proximal portion (133) as shown in FIG. 16. A second discrete position for distal portion (131) is an angled or curved orientation relative to proximal portion (133) where distal portion (131) bends or angles downward toward lower jaw (16, 216) of the associated end effector. Of course in some other versions, the second discrete position for distal portion (131) could be flared or bent upward relative to proximal portion (133). In view of the teachings herein, other configurations and ways to achieve such configurations for a tip (119) having multiple rotatable pinned sections will be apparent to those of ordinary skill in the art.

B. Exemplary End Effector Pivoting Tip with Fulcrum Feature

Figure 17:
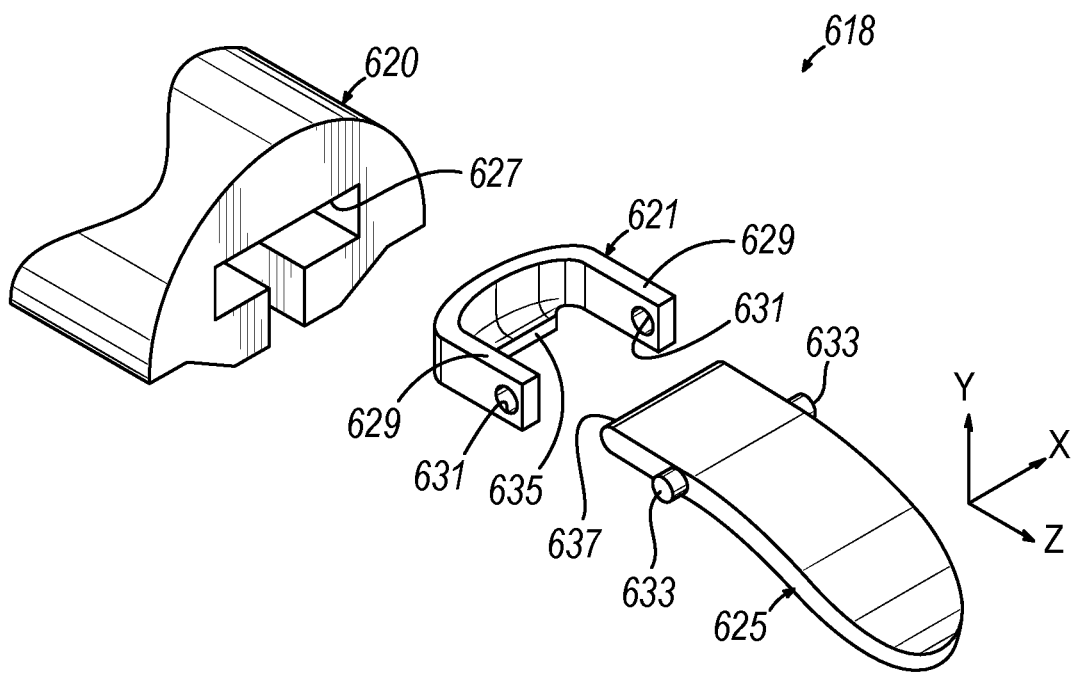
FIG. 17 depicts a perspective view of an alternate anvil of an end effector for use with the surgical instruments described herein.
Figure 18:
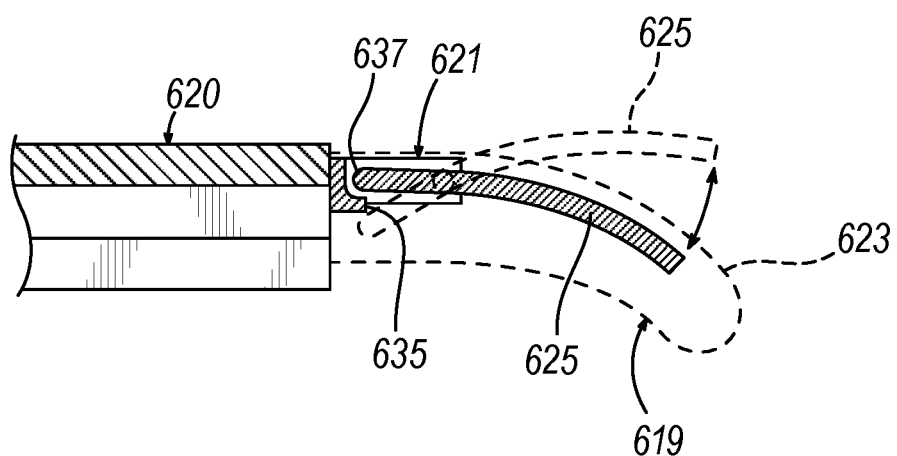
FIG. 18 depicts a cross sectional side view of the anvil of FIG. 17, shown with the elastomeric overmold in phantom, and showing a pivot member pivotable about a fulcrum feature.

FIGS. 17 and 18 depict a portion of an exemplary anvil (618) that is usable with the end effectors described herein and others. For instance, anvil (618) can be interchanged or used in place of anvils (18, 218, 318) of respective end effectors (12, 212, 312, 412) described above. It will be appreciated that end effectors (12, 212, 312, 412) incorporating anvil (618) may be used with instruments (10, 310) and the other surgical instruments described herein. To this extent, end effectors (12, 212, 312, 412) incorporating anvil (618) may be integrally formed with instruments (10, 310) and the other surgical instruments described herein, or in the alternative may be interchangeable end effectors of instruments (10, 310) and the other surgical instruments described herein.

As part of any of end effectors (12, 212, 312, 412), anvil (618) is operable to pivot relative to lower jaws (16, 216). Anvil (618) and lower jaws (16, 216) may clamp tissue (90) similarly to clamping performed by anvil (18) and lower jaw (16) shown in FIG. 7. Anvil (618) and lower jaws (16, 216) may further cut and staple clamped tissue (90) similarly to the cutting and stapling performed by anvil (18) and lower jaw (16) shown in FIG. 7. To accomplish the cutting and stapling, as described above, end effectors (12, 212, 312, 412) incorporating anvil (618) further comprises a cartridge (37, 237) containing staples where cartridge (37, 237) is operable to be placed in lower jaw (16, 216).

Anvil (618) comprises body (620), tip (619), and connection member (621). Tip (619) comprises a polymeric or metallic covering (shown as an elastomeric overmold (623)) and a pivot member (625) as best seen in FIG. 18. Connection member (621) is configured to attach with body (620). In one version connection member (621) comprises a metal stamping configured to be welded to body (620) of anvil (618). In another version, connection member (621) is configured to be press-fit or clicked to body (620). In such versions, connection member (621) may comprise features that engage with slot (627) of body (620). In view of the teachings herein, other ways to attach connection member (621) with body (620) of anvil (618) will be apparent to those of ordinary skill in the art.

Connection member (621) comprises arms (629) that extend distally. Arms (629) each comprise bores (631) that are configured to receive projections (633) of pivot member (625). In this manner, bores (631) provides a pivot axis or axis of rotation for tip (619). Connection member (621) further comprises a curved lip (635) that acts like a fulcrum feature. Curved lip (635) protrudes distally and is configured to interact with a proximal end (637) of pivot member (625) of tip (619).

Pivot member (625) is connectable with connection member (621) as mentioned, with projections (633) being received within bores (631) of connection member (621). With this configuration, pivot member (625) is rotatably adjustable relative to connection member (621) and body (620) of anvil (618). When projections (633) are within bores (631), proximal end (637) of pivot member (625) is located in a slight overlapping orientation relative to curved lip (635). The remainder of pivot member (625) extends distally from connection member (621). As shown in FIG. 18, elastomeric overmold (623), shown in phantom to reveal internal components, covers pivot member (625) and connection member (621).

With the above configuration for anvil (618), tip (619) is configured to rotate or pivot about the pivot axis defined by bores (631), whereby proximal end (637) of pivot member (625) can adopt discrete positions relative to curved lip (635), such that tip (619) adopts discrete positions relative body (620). For instance, as shown in FIG. 18 by the solid lines illustrating pivot member (625), in a first position, pivot member (625) can have an angled orientation. In the illustrated version, this corresponds to when proximal end (637) of pivot member (625) is above curved lip (635). As shown in FIG. 18 by the broken lines illustrating pivot member (625), in a second position, pivot member (625) can have a straight or slightly flared orientation. In the illustrated version, this corresponds to when proximal end (637) of pivot member (625) is below curved lip (635).

In the present example, elastomeric overmold (623) acts as the spring that holds pivot member (625) in place on either side of curved lip (635) until a sufficient force is applied to tip (619) to overcome the bias provided by elastomeric overmold (623) and the contact between proximal end (637) and curved lip (635). For instance, when in the angled orientation, when a sufficient upward force is applied to tip (619), proximal end (637) of pivot member (625) will rotate downward and click past curved lip (635) allowing tip (619) to adopt the other discrete position. Similarly, when in the straight or flared orientation, when a sufficient downward force is applied to tip (619), proximal end (637) of pivot member (625) will rotate upward and click past curved lip (635) allowing tip (619) to adopt the other discrete position.

In the present example, proximal end (637) is rounded and toleranced so that it clicks past curved lip (635), which acts as the fulcrum feature. In some other versions, curved lip (635) can incorporate a rounded and toleranced distal end to facilitate movement of proximal end (637) from one side of curved lip (635) to the other side of curved lip (635). Again, as mentioned, once on either side of curved lip (635) or other fulcrum feature, tip (619) will remain in place because of elastomeric overmold (623) acting as the spring to hold pivot member (625) in place.

In one version of anvil (618), tuning for force or sound feedback could be accomplished by configuring the fulcrum feature with a deformable dome-type geometry that proximal end (637) moves past when changing discrete positions. In other words, greater or lesser deformation can be used with the fulcrum feature so that a user gets haptic and/or audible feedback confirming tip (619) has changed position. In view of the teachings herein, other ways to modify anvil (618), connection member (621), and tip (619) to achieve a pivoting tip that adopts discrete positions will be apparent to those of ordinary skill in the art.

C. Exemplary End Effector Pivoting Tip with Triangular Pivot Member

Figure 19:
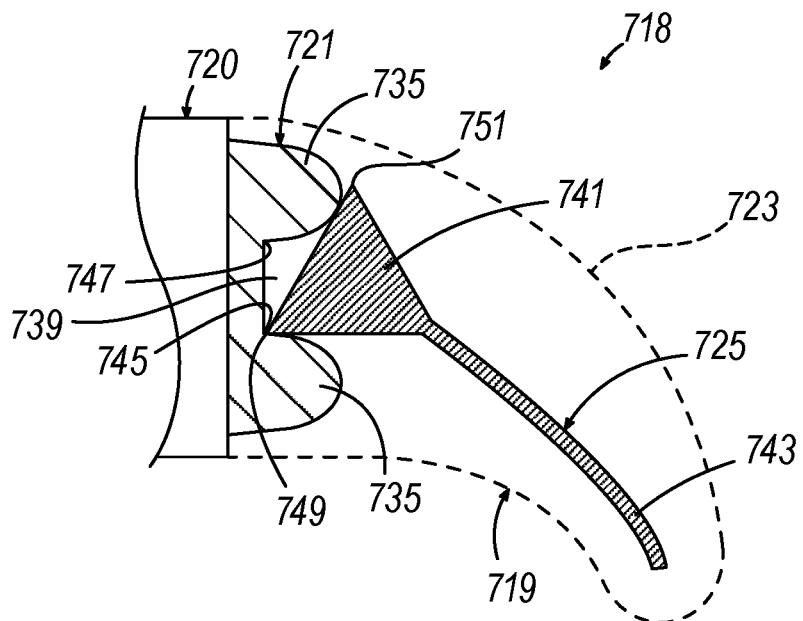
FIG. 19 depicts a perspective view of an alternate tip of an anvil of an end effector for use with the surgical instruments described herein, shown with the tip in a first position.
Figure 20:
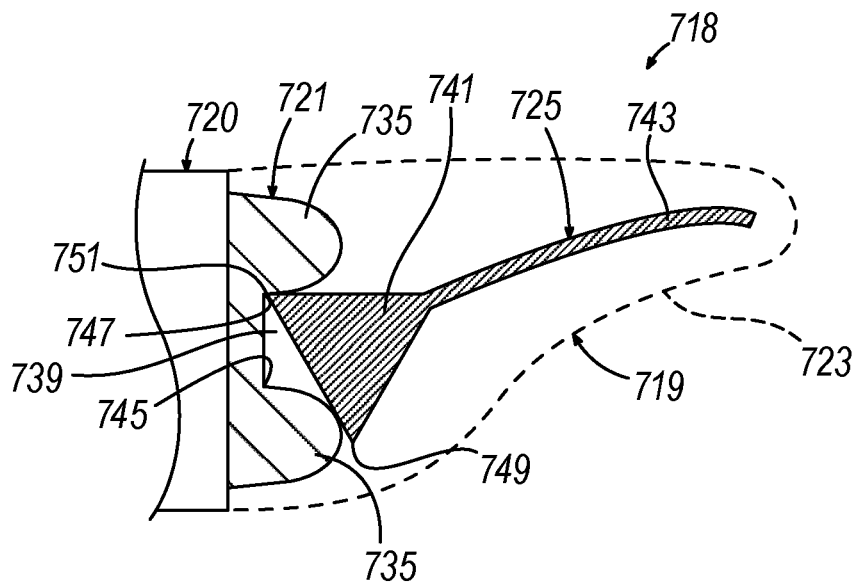
FIG. 20 depicts a perspective view of the tip of FIG. 19, shown with the tip in a second position.

FIGS. 19 and 20 depict a portion of an exemplary anvil (718) that is usable with the end effectors described herein and others. For instance, anvil (718) can be interchanged or used in place of anvils (18, 218, 318) of respective end effectors (12, 212, 312, 412) described above. It will be appreciated that end effectors (12, 212, 312, 412) incorporating anvil (718) may be used with instruments (10, 310) and the other surgical instruments described herein. To this extent, end effectors (12, 212, 312, 412) incorporating anvil (718) may be integrally formed with instruments (10, 310) and the other surgical instruments described herein, or in the alternative may be interchangeable end effectors of instruments (10, 310) and the other surgical instruments described herein.

As part of any of end effectors (12, 212, 312, 412), anvil (718) is operable to pivot relative to lower jaws (16, 216). Anvil (718) and lower jaws (16, 216) may clamp tissue (90) similarly to clamping performed by anvil (18) and lower jaw (16) shown in FIG. 7. Anvil (718) and lower jaws (16, 216) may further cut and staple clamped tissue (90) similarly to the cutting and stapling performed by anvil (18) and lower jaw (16) shown in FIG. 7. To accomplish the cutting and stapling, as described above, end effectors (12, 212, 312, 412) incorporating anvil (718) further comprises a cartridge (37, 237) containing staples where cartridge (37, 237) is operable to be placed in lower jaw (16, 216).

Anvil (718) comprises body (720), tip (719), and connection member (721). Tip (719) comprises a polymeric or metallic covering (shown as an elastomeric overmold (723)) and a pivot member (725). Connection member (721) is configured to attach with body (720). In one version connection member (721) comprises a metal stamping configured to be welded to body (720) of anvil (718). In another version, connection member (721) is configured to be press-fit or clicked to body (720). In such versions, connection member (721) may comprise features that engage with a slot of body (720), similar to slot (627) of body (620). In view of the teachings herein, other ways to attach connection member (721) with body (720) of anvil (718) will be apparent to those of ordinary skill in the art.

Connection member (721) comprises a dual bump feature (735) that extends distally. As shown in the illustrated version, connection member (721) further comprises a space or gap (739) between the bumps of dual bump feature (735). In the present example, but not required in all versions, dual bump feature (735) is rigid. Pivot member (725) comprises triangular body (741) and elongated member (743) connected with and extending distally from triangular body (741). In the present example, but not required in all versions, pivot member (725) comprises a metallic structure.

In the present example, dual bump feature (735) is dimensioned and toleranced to interact with triangular body (741) of pivot member (725). For instance, dual bump feature (735) defines base corners (745, 747), and triangular body (741) defines vertexes (749, 751). As shown in FIG. 19, when tip (719) is in a first discrete position where tip (719) has a downward angled orientation, vertex (749) is biased into base corner (745). At the same time, vertex (751) is pivoted away from base corner (747) and is instead near a distal end of dual bump feature (735). As shown in FIG. 20, when tip (719) is in a second discrete position where tip (719) has a straight or upward angled orientation, vertex (751) is biased into base corner (747). At the same time, vertex (749) is pivoted away from base corner (745) and is near a distal end of dual bump feature (735).

In the present example, elastomeric overmold (723) biases triangular body (741) proximally. Thus, elastomeric overmold (723) acts as the spring that holds triangular body (741) of pivot member (725) in place against dual bump feature (735). However, when a sufficient force is applied to tip (719) to overcome the proximal bias imposed by elastomeric overmold (723), triangular body (741) pivots between dual bump feature (735) as illustrated by the change in position of triangular body (741) in FIGS. 19 and 20. For instance, when in the angled or curved orientation, shown in FIG. 19, when a sufficient upward and/or distally directed force is applied to tip (719), vertex (749) of triangular body (741) travels distally along a lower bump of dual bump feature (735). Meanwhile, vertex (751) of triangular body (741) of pivot member (725) travels proximally along an upper bump of dual bump feature (735) until locking into base corner (747). Similarly, when in the straight or upward bent orientation shown in FIG. 20, when a sufficient downward and/or distally directed force is applied to tip (719), vertex (749) of triangular body (741) travels proximally along a lower bump of dual bump feature (735) until locking into base corner (745). Meanwhile, vertex (751) of triangular body (741) of pivot member (725) travels distally along an upper bump of dual bump feature (735). In one version, toggling the position of tip (719) may involve a user pinching and pulling distally on tip (719) thereby temporarily deforming elastomeric overmold (723) when relocating tip (719). Still in other versions, toggling the position of tip (719) may involve a user pushing upward or downward such that the force is largely orthogonally applied to the longitudinal axis of anvil (718).

D. Exemplary Anvil with Swiveling Tip

In some instances, it may be desirable to provide the anvil of a surgical stapler end effector with a selectively adjustable distal tip that is configured to transition between first and second discrete positions via rotation about a longitudinal axis. Such configurations may provide different benefits than other configurations in which the distal trip transitions between first and second discrete positions via upward and downward pivoting about a lateral axis as described above in connection with FIGS. 13-20, or via flexion as described in U.S. patent application Ser. No. 16/729,559, entitled "Surgical Stapler with Deflectable Distal Tip," filed on Dec. 30, 2019, published as U.S. Pub. No. 2020/0237370 on Jul. 30, 2020, the disclosure of which is incorporated by reference herein. Advantageously, in such versions the anvil tip may be configured with a rigid construction, an elastically deformable construction, or any suitable combination thereof while still be selectively transitionable between first and second discrete positions exhibiting the advantages described above. Furthermore, in some instances, it may be desirable to rotatably couple the anvil tip with the anvil body such that the tip is rotatable about an axis that extends in a vertical plane containing the longitudinal axes of the anvil body and the opposing lower jaw of the end effector. In such versions, the anvil tip is said to rotatably "swivel" relative to the anvil body between the first and second discrete positions.

FIGS. 21-29 depict exemplary anvils (1218, 1318, 1418, 1518, 1618, 1718, 1818) having distal tips (1222, 1322, 1422, 1522, 1622, 1722, 1822) that are selectively rotatable relative to the respective anvil body in such a manner that the tip (1222, 1322, 1422, 1522, 1622, 1722, 1822) is configured to swivel relative to the anvil body between first and second discrete positions. Anvils (1218, 1318, 1418, 1518, 1618, 1718, 1818) and their respective end effectors described below may be interchanged with any of the exemplary anvils (18, 218, 318, 518, 618, 718) and end effectors (12, 212, 312, 412) described above, and may be used with surgical instruments (10, 310) and other exemplary surgical instruments described herein. It will be understood that anvils (1218, 1318, 1418, 1518, 1618, 1718, 1818) are similar to anvils (18, 218, 318, 518, 618, 718) described above in that anvils (1218, 1318, 1418, 1518, 1618, 1718, 1818) are operable to clamp tissue (90) against a staple cartridge supported within the lower jaw of a corresponding end effector, such as staple cartridge (37) supported within lower jaw (16) described above, and are further operable to form staples ejected by the staple cartridge into the clamped tissue. As described below, anvils (1218, 1318, 1418, 1518, 1618, 1718, 1818) may be provided with a tip locking mechanism operable to releasably retain the anvil tip within the discrete positions and thereby protect against inadvertent rotation of the anvil tip out of a discrete position.

It will be appreciated that any of the exemplary anvil tips (1222, 1322, 1422, 1522, 1622, 1722, 1822) described below may be formed of one or more materials as desired, which may include rigid materials, elastically deformable materials, or combinations thereof. For instance, in some versions an anvil tip (1222) may be include a core or proximal base portion formed of a rigid material such as a metal, and an elastomeric body portion coupled to or otherwise overmolded about the rigid core or proximal base portion.

1. Overview of Exemplary Anvil with Swiveling Tip

Figure 21:
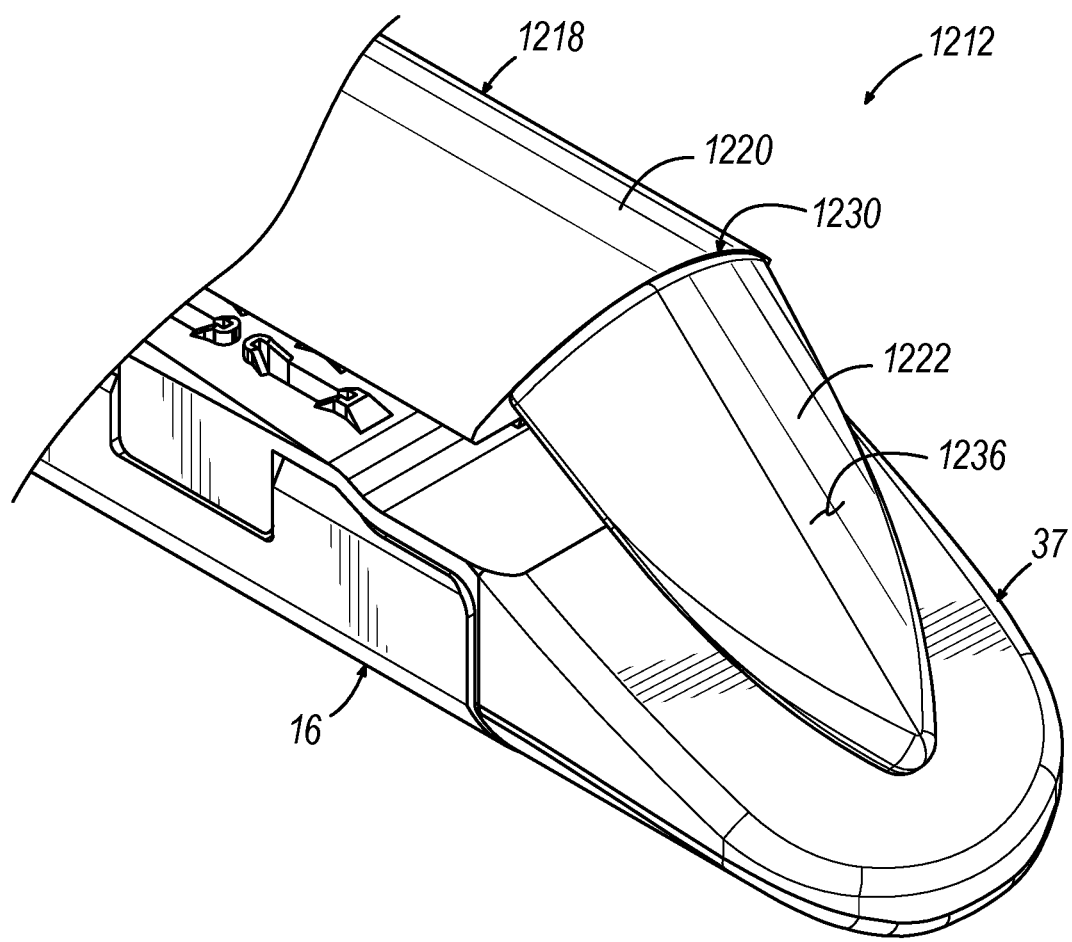
FIG. 21 depicts a perspective view of a distal portion of another exemplary end effector having an anvil with a selectively rotatable distal tip, showing the distal tip in a first discrete position relative to an anvil body.
Figure 22:
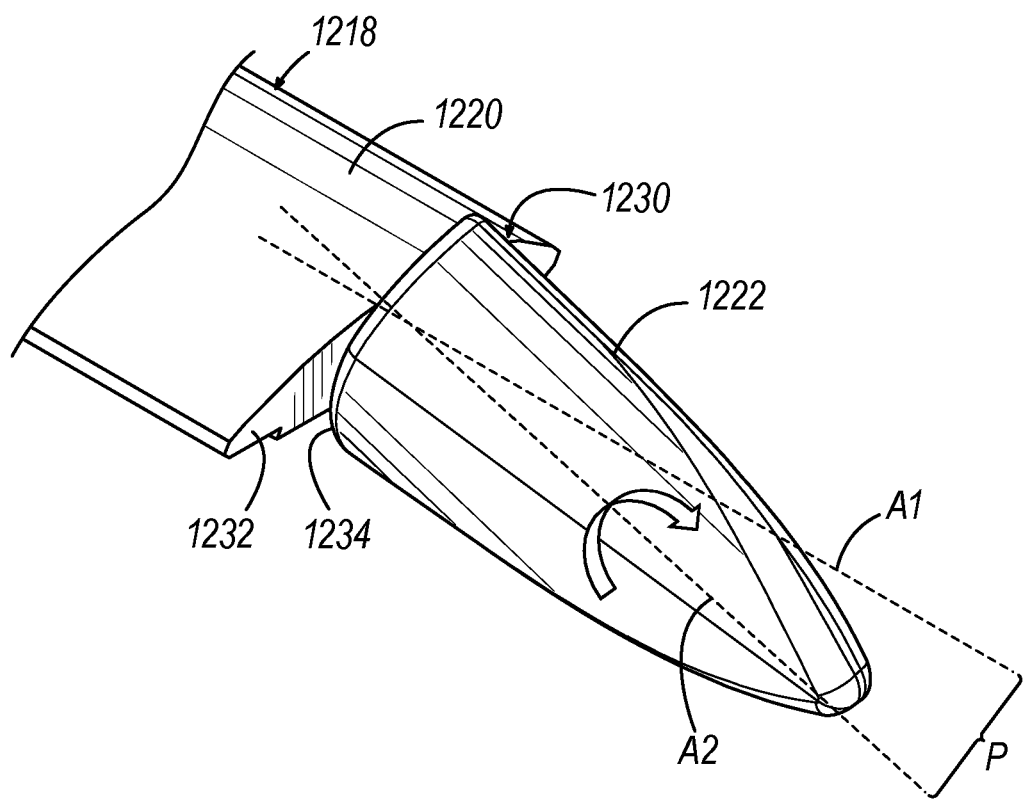
FIG. 22 depicts a perspective view of the body and the distal tip of the anvil of FIG. 21, showing the distal tip rotating relative to the body between the first discrete position and a second discrete position.
Figure 23A:
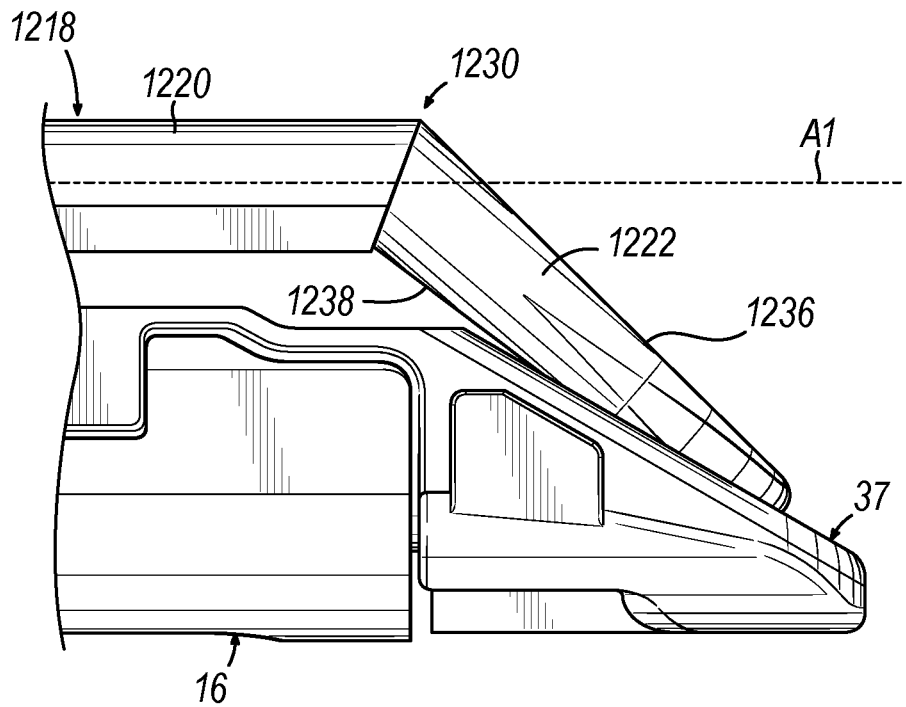
FIG. 23A depicts a side elevational view of a distal portion of the end effector of FIG. 21, showing the distal tip in the first discrete position relative to the body.
Figure 23B:
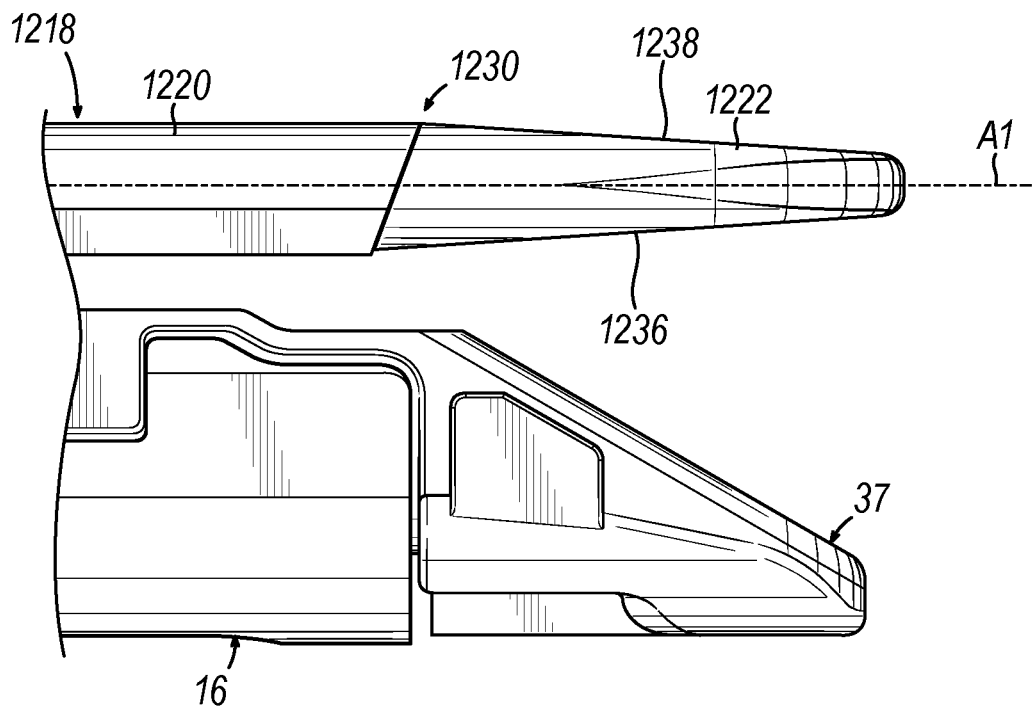
FIG. 23B depicts a side elevational view of a distal portion of the end effector of FIG. 21, showing the distal tip in the second discrete position relative to the body.

FIGS. 21-23B illustrate an exemplary end effector (1212) that includes an anvil (1218) pivotably coupled with lower jaw (16), and staple cartridge (37) positioned within lower jaw (16). Anvil (1218) includes an elongate anvil body (1220) having a plurality of staple forming pockets (not shown) similar to pockets (53) of anvil (18) arranged along a length thereof. A tapered distal anvil tip (1222) is rotatably coupled to a distal end of anvil body (1220), and is selectively rotatable relative to anvil body (1220) between first and second discrete positions in response to an external rotational force applied to tip (1222) by a user or by an adjacent anatomical structure. As shown in FIGS. 21 and 23A, anvil tip (1222) in the first discrete position is angled relative to anvil body (1220) such that a distal end of anvil tip (1222) extends toward staple cartridge (37) and is configured to contact a distal end of staple cartridge (37) when anvil (1218) is closed to clamp tissue therebetween. As shown in FIG. 23B, anvil tip (1222) in the second discrete position is oriented straight relative to anvil body (1220) such that when end effector (1212) is in the closed state, anvil tip (1222) extends generally parallel to lower jaw (16) and staple cartridge (37), and the distal end of anvil tip (1222) is thus spaced apart from the distal end of staple cartridge (37) to define a gap therebetween. Thus, anvil tip (1222) in the straight position is configured to provide end effector (1212) with a distally opening aperture throughout its clamping range that is larger than a corresponding aperture exhibited by end effector (1212) when anvil tip (1222) is in angled position. Accordingly, similar to other exemplary versions described above, anvil tip (1222) in the angled position is suitably oriented to draw tissue proximally between anvil (1218) and staple cartridge (37) and to facilitate visualization of the target tissue during closure of end effector (1212). Additionally, anvil tip (1222) in the straight position is suitably oriented to facilitate marching during a stapling procedure, as also described above. A user may thus select the angled position or the straight position of anvil tip (1222) as desired to best facilitate a particular procedure being performed.

As shown in FIG. 22, anvil body (1220) extends along a longitudinal body axis (A1), and anvil tip (1222) is configured to rotate about a rotational axis (A2) that intersects and is obliquely angled relative to body axis (A1) while still extending in a generally proximal-to-distal direction. Axes (A1, A2) thus define and are contained by a vertical plane (P) that extends along a longitudinal centerline of end effector (1212), so as to also contain a longitudinal axis (not shown) of lower jaw (16). In other words, each axis (A1, A2) extends within and along vertical plane (P). The rotational axis (A2) of anvil tip (1222) is defined by a rotary member (not shown), which may be in the form of a shaft similar to any of shafts (1324, 1524, 1634, 1740) described below in connection with exemplary anvils (1318, 1518, 1618, 1718) of FIGS. 24-32. In the present version, the rotary member is suitably configured such that rotational axis (A2) extends obliquely to the longitudinal axis of anvil tip (1222).

As shown in FIGS. 22-23B, anvil (1218) includes an angled interface (1230) defined by an angled distal face (1232) of anvil body (1220) and an angled proximal face (1234) of anvil tip (1222). Angled faces (1232, 1234) are configured to engage one another in first and second mating configurations to define the first and second discrete positions of anvil tip (1222). As shown in FIGS. 23A and 23B, angled faces (1232, 1234) are obliquely angled relative to the longitudinal axes of anvil body (1220) and anvil tip (1222). As shown in FIG. 23A, the oblique angles of angled interface (1230) are summated when anvil tip (1222) is in the first rotational orientation relative to anvil body (1220), thus orienting the longitudinal axis of anvil tip (1222) obliquely relative to the longitudinal axis (A1) of anvil body (1220) to provide anvil tip (1222) in the angled position. The anvil tip (1222) includes first and second opposing surfaces (1236, 1238) that are shown as being generally arcuate. In the first rotational orientation of FIG. 23A, first surface (1236) is the outer surface, and first surface (1238) is the inner surface relative to staple cartridge (37).

The second rotational orientation may be obtained by rotating anvil tip (1222) 180-degrees relative to the first rotational orientation. As shown in FIG. 23B, the oblique angles of angled interface (1230) are configured to negate one another when anvil tip (1222) is in the second rotational orientation relative to anvil body (1220), thus aligning the longitudinal axes of anvil body (1220) and anvil tip (1222) coaxially such that anvil tip (1222) extends distally straight from anvil body (1220). In other words, angled faces (1232, 1234) are oriented relative to one another in the second discrete position, shown in FIG. 23B, such that angled faces (1232, 1234) define supplementary angles that together define a 180-degree angle. In other versions, angled faces (1232, 1234) could be alternatively configured to define an angle of greater than 180 degrees when anvil tip (1222) is in the second discrete position. In such versions, anvil tip (1222) in the second discrete position would flare upwardly away from the distal end of staple cartridge (37) and anvil body axis (A1). In the second rotational orientation of FIG. 23B, second surface (1238) is the outer surface, and first surface (1236) is the inner surface relative to staple cartridge (37).

Though not shown, anvil (1218) may further include a tip locking mechanism operable to releasably retain anvil tip (1222) in the first and second discrete positions, and thus prevent inadvertent rotation of tip (1222) away from a selected position. Such a tip locking mechanism may comprise one or more detent features, protrusions, recesses, resilient members, interference features, and the like of various types that will be readily apparent to those of ordinary skill in the art in view of the teachings herein. For instance, anvil (1218) may include any one or more of the exemplary tip locking mechanisms described below in connection with anvils (1318, 1418, 1518, 1618, 1718, 1818), such as detent protrusions (1340) and detent recesses (1342). Additionally, though not shown, anvil (1218) may further include a connection member rigidly secured to a distal end of anvil body (1220) and to which anvil tip (1222) is rotatably coupled. Such a connection member may be similar to any of the exemplary connection members (1330, 1430, 1530, 1630, 1730, 1830) described below. Moreover, anvil tip (1222) may be secured axially relative to anvil body (1220) using any of the exemplary methods described below.

2. Anvil with Swiveling Tip Having Tip Locking Mechanism with Detent Bumps

Figure 24:
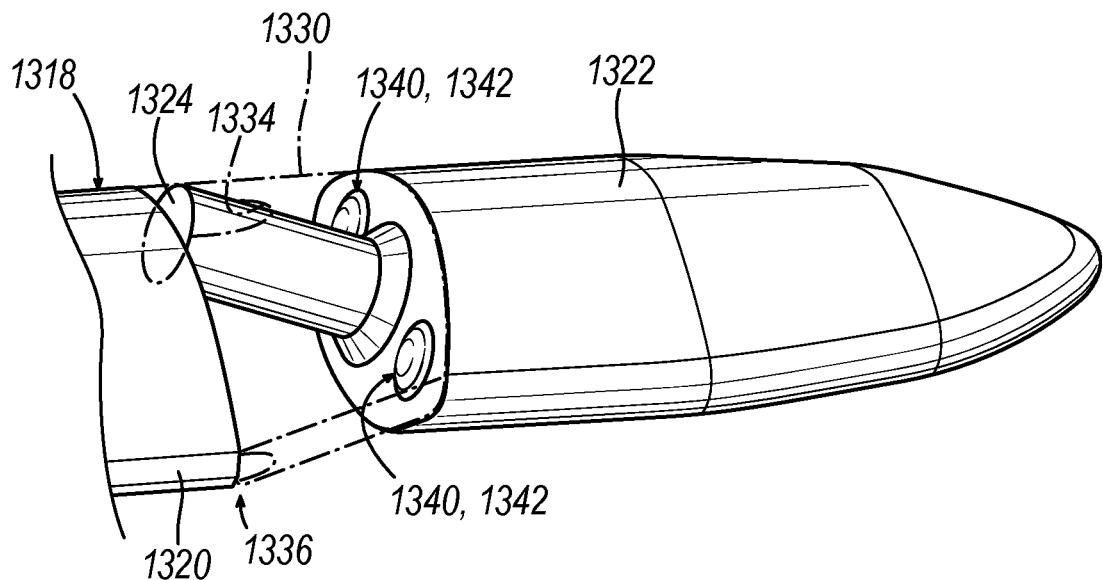
FIG. 24 depicts a perspective view of a distal portion of another exemplary anvil having a body, a selectively rotatable distal tip, and a tip locking mechanism, showing the distal tip in a pre-finalized state of assembly and in a second discrete position relative to the body.
Figure 25:
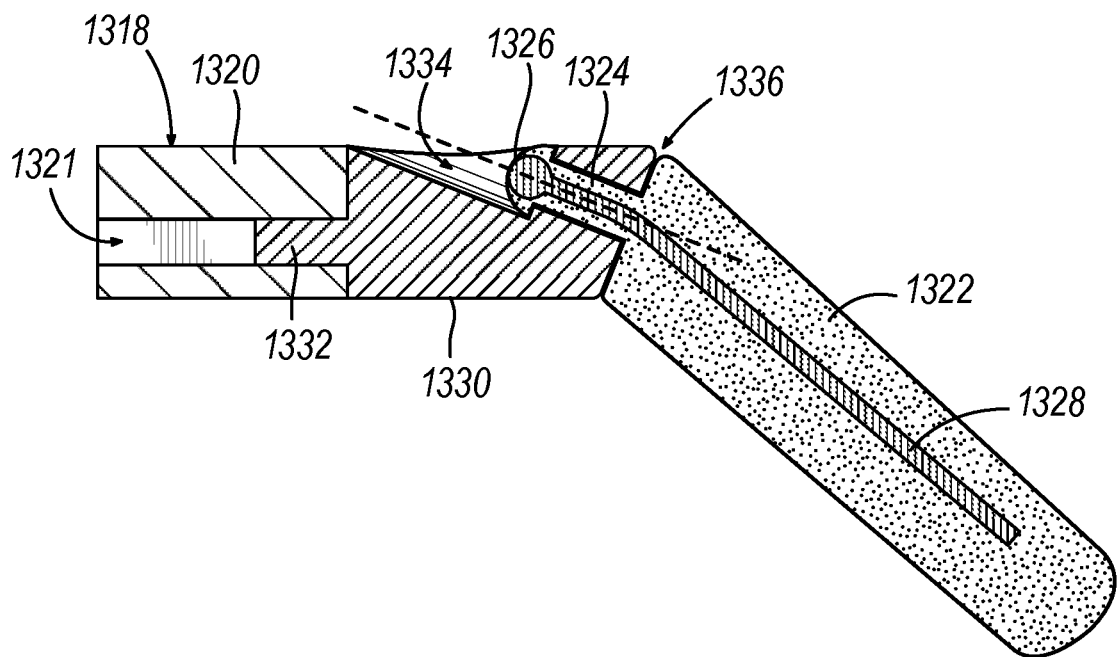
FIG. 25 depicts a side sectional view of the distal portion of the anvil of FIG. 24, showing the distal tip in a finalized state of assembly and in a first discrete position relative to the body.

FIGS. 24-25 illustrate a distal portion of another exemplary anvil (1318) suitable for use with any of the exemplary end effectors described above. Anvil (1318) is similar to anvil (1218) described above except as otherwise described below. Like anvil (1218), anvil (1318) includes an elongate anvil body (1320) having a plurality of staple forming pockets (not shown) arranged along an underside thereof, and a tapered distal tip (1322) rotatably disposed at a distal end of anvil body (1320). Like anvil tip (1222), anvil tip (1322) is configured to swivel relative to anvil body (1320) about a rotational axis disposed within a plane that contains the longitudinal axis of anvil body (1320) and a longitudinal centerline of a corresponding end effector having lower jaw (16). In particular, anvil tip (1322) is configured to swivel about the rotational axis between a first discrete position in which anvil tip (1322) is angled relative to anvil body (1320) in a direction toward lower jaw (16), and a second discrete position in which anvil tip (1322) extends distally straight from anvil body (1320) so as to be oriented away from lower jaw (16).

Anvil (1318) further includes a connection member (1330) that is rigidly secured to a distal end of anvil body (1320) and rotatably supports anvil tip (1322). As seen in FIG. 25, connection member (1330) includes a proximal plug (1332) that is securely received (e.g., via an interference fit) within an open distal end of a longitudinal anvil slot (1321) of anvil body (1320), which may be similar to longitudinal anvil slot (42) of anvil (18) described above. Connection member (1330) further includes an internal bore (1334) that extends obliquely to a longitudinal axis of anvil body (1320) and connection member (1330), and is configured to rotatably receive a proximally extending shaft (1324) of anvil tip (1322). Shaft (1324) may be formed integrally with a body of anvil tip (1322) and extends obliquely to a longitudinal axis thereof. Bore (1334) and shaft (1324) cooperate to define a rotational axis (A2) of anvil tip (1322) that is obliquely angled relative to the longitudinal axes of anvil body (1320) and anvil tip (1322). Anvil tip (1322) and connection member (1330) include angled end faces that adjustably mate with one another to define an angled interface (1336) that provides for the angled and straight orientations of anvil tip (1322) relative to anvil body (1320) in the first and second discrete positions, similar to angled interface (1230) of anvil (1218) described above.

A proximal end of shaft (1324) of anvil tip of anvil tip (1322) of the present version includes a retention feature (1326) configured to engage an internal shoulder of bore (1334) and thereby retain shaft (1324) axially within bore (1334) while still permitting shaft (1324) to rotate therein to enable rotation of anvil tip (1322) between the straight and angled positions. Retention feature (1326) of the present example is shown in FIG. 25 the form of a rounded protrusion, which may be formed through deformation (e.g., thermal deformation, or "heat staking") of the proximal end of shaft (1324) following its insertion into bore (1334) during initial assembly of anvil (1318). In that regard, FIG. 24 shows anvil (1318) in a pre-finalized state of assembly prior to the formation of rounded protrusion (1326), and FIG. 25 shows anvil (1318) in a finalized state of assembly following deformation of rounded protrusion (1326). Various other suitable types of retention features that may be provided integrally with or independently from shaft (1324) will be readily apparent to those of ordinary skill in the art in view of the teachings herein.

As shown in FIG. 25, anvil tip (1322) of the present example further includes an optional stiffening member (1328) embedded therein and which extends proximally through shaft (1324) and distally through a least a portion of a body of anvil tip (1322). Stiffening member (1328) may be formed of a material having greater rigidity than the body of anvil tip (1322), such that a distal-most portion of anvil tip (1322) through which stiffening member (1328) does not extend has greater flexibility that a proximal portion of anvil tip (1322), including shaft (1324). In some versions, the body of anvil tip (1322) may be formed of a flexible elastomeric material while stiffening member (1328) is formed of a more rigid material, which may be bendable. In some versions, the material of stiffening member (1328) may compatible with magnetic resonance imaging (MRI) devices, and/or may be configured to serve as a marker for fluoroscopic identification. In the present version, a proximal end of stiffening member (1328) joins within an inner core element of retention feature (1326), thus enabling retention feature (1326) to maintain its engagement with the inner shoulder of bore (1334) when an axial load is exerted on shaft (1324), for instance during swiveling of anvil tip (1322).

As shown best in FIG. 24, anvil (1318) further includes a tip locking mechanism configured to releasably retain anvil tip (1322) in the first and second discrete positions. The tip locking mechanism of the present example is shown in the form of detent features provided at angled interface (1336) of anvil tip (1322) and connection member (1330). In particular, a pair of detent protrusions (1340) is provided on the angled proximal face of anvil tip (1322), and a corresponding pair of detent recesses (1342) is provided in the angled distal face of connection member (1330). Detent protrusions (1340) are configured to fully seat within detent recesses (1342) when anvil tip (1322) is in either of the first or second discrete positions. Detent protrusions (1340)

and/or shaft (1324) may resiliently deform as anvil tip (1322) is rotated between the discrete positions to permit detent protrusions (1340) to temporarily disengage detent recesses (1342). Upon anvil tip (1322) reaching one of the first or second discrete positions relative to anvil body (1320), detent protrusions (1340) then snap back into respective detent recesses (1342), thus providing the user with tactile confirmation that anvil tip (1322) has fully assumed the selected tip position. In place of or in addition to detent protrusions (1340) and/or detent recesses (1342), anvil (1318) may include various other suitable types of tip locking mechanisms, such as those described below.

3. Anvil with Swiveling Tip Having Tip Locking Mechanism with Detent Arms

Figure 26:
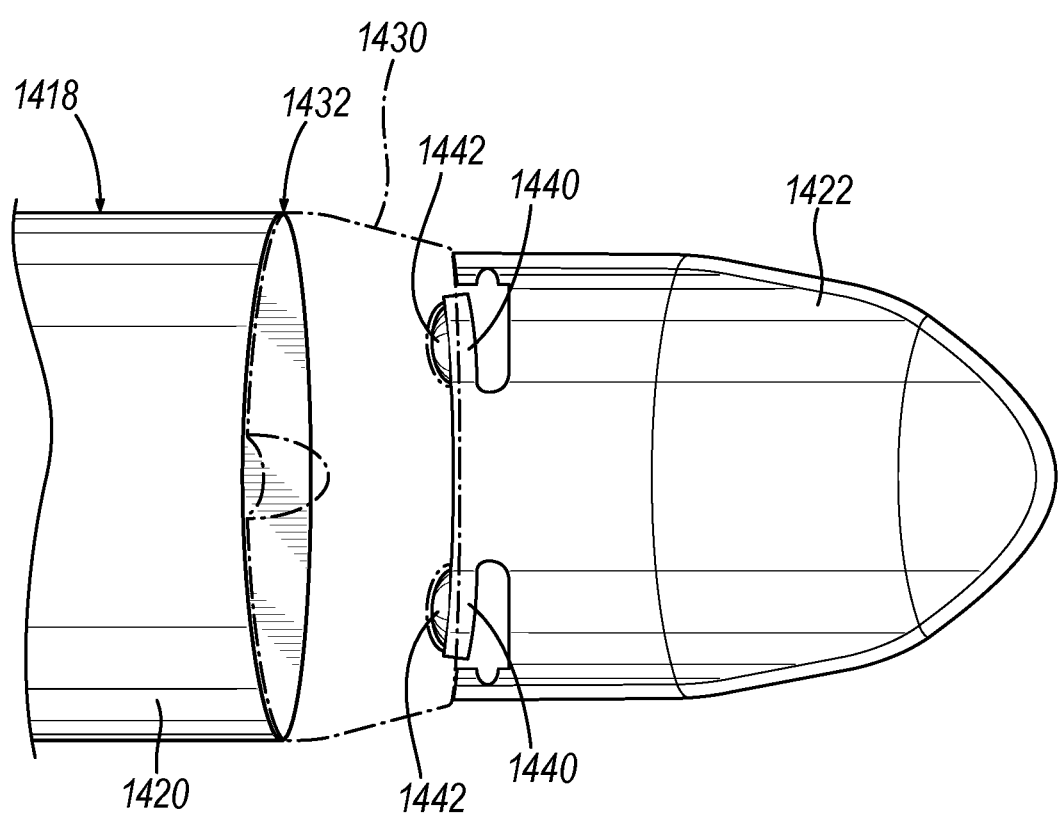
FIG. 26 depicts a top plan view of a distal portion of another exemplary anvil having a body, a selectively rotatable distal tip, and a tip locking mechanism, showing the distal tip in a first discrete position relative to the body.

FIG. 26 shows a distal portion of another exemplary anvil (1418) suitable for use with any of the exemplary end effectors described above. Anvil (1418) is similar to anvil (1318) described above except as otherwise described below. Like anvil (1318), anvil (1418) includes an elongate anvil body (1420) having a plurality of staple forming pockets (not shown) arranged along an underside thereof, a connection member (1430) secured to a distal end of anvil body (1420), and a tapered distal tip (1422) rotatably coupled to connection member (1430). Like anvil tip (1322), anvil tip (1422) is configured to swivel relative to connection member (1430) and anvil body (1420) about a rotational axis disposed within a plane that contains the longitudinal axis of anvil body (1420) and a longitudinal centerline of a corresponding end effector having lower jaw (16). In particular, anvil tip (1422) is configured to swivel about the rotational axis between a first discrete position in which anvil tip (1422) is angled relative to anvil body (1420) in a direction toward lower jaw (16), and a second discrete position in which anvil tip (1422) extends distally straight from anvil body (1420) so as to be oriented away from lower jaw (16). Connection member (1430) and anvil tip (1422) define an angled interface (1432) therebetween that provides for the angular reorientation of anvil tip (1322) relative to the longitudinal axis of anvil body (1420) during rotation of anvil tip (1422) between the first and second discrete positions.

Anvil (1418) of the present example further includes a tip locking mechanism disposed at angled interface (1432) and configured to releasably retain anvil tip (1422) in each of the first and second discrete positions relative to anvil body (1420). The present tip locking mechanism is shown in the form of a pair of resilient detent arms (1440) extending laterally from the angled proximal end of anvil tip (1422), and a corresponding pair of detent recesses (1442) disposed on the angled distal face of connection member (1430). Detent arms (1440) are configured to seat within detent recesses (1442) when anvil tip (1422) is in either of the first or second discrete positions. As anvil tip (1422) is rotated relative to anvil body (1420), detent arms (1440) resiliently deflect distally to thereby disengage detent recesses (1442). As anvil tip (1422) reaches one of the first or second discrete positions, detent arms (1440) snap back into respective detent recesses (1442), thus providing the user with tactile confirmation that anvil tip (1422) has fully assumed the selected tip position.

Figure 27A:
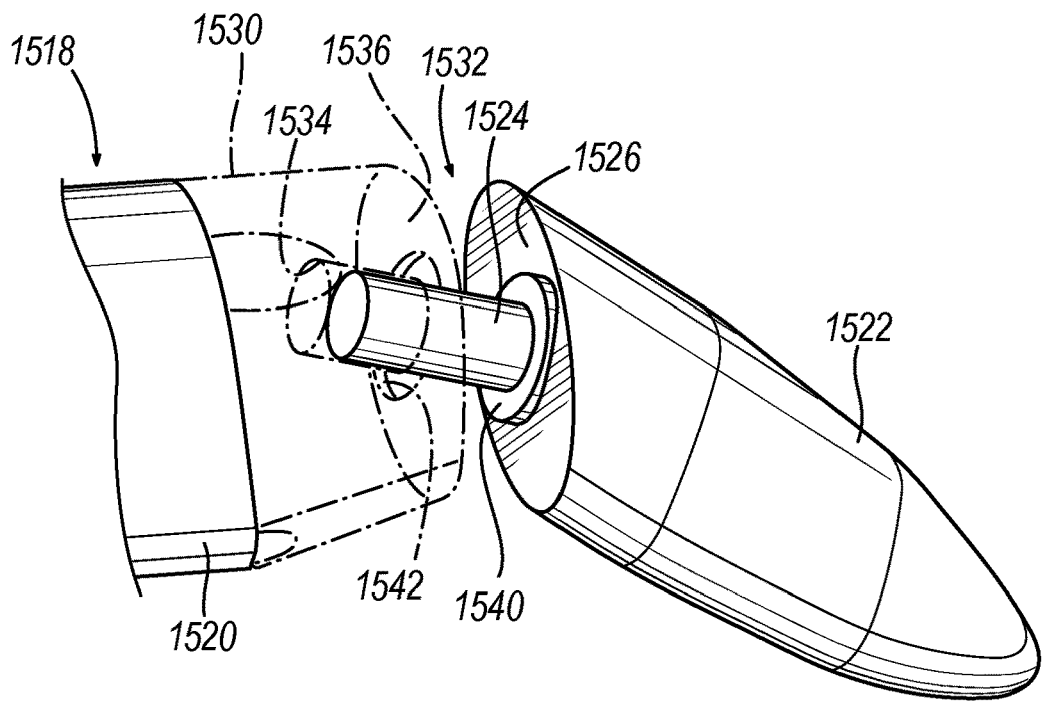
FIG. 27A depicts a perspective of a distal portion of another exemplary anvil having a body, a rotatable distal tip, and a tip locking mechanism, showing the distal tip partially decoupled from and in a second discrete position relative to the body.
Figure 27B:
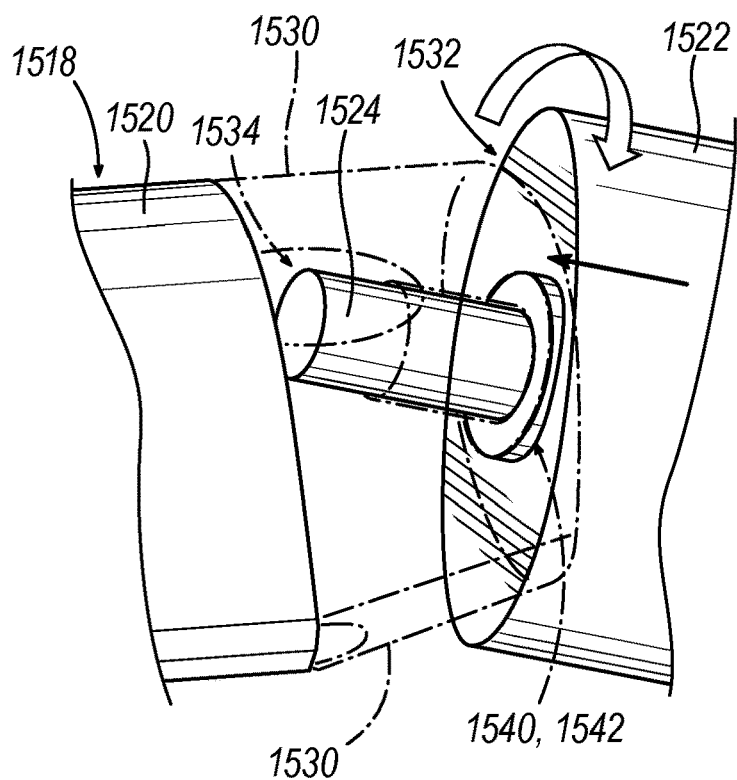
FIG. 27B depicts an enlarged perspective view of the distal portion of the anvil of FIG. 27A, showing the distal tip rotating relative to the body between a first discrete position and the second discrete position.

4. Anvil with Swiveling Tip Having Tip Locking Mechanism with Annular Wave Feature FIGS. 27A-27B show a distal portion of another exemplary anvil (1518) suitable for use with any of the exemplary end effectors described above. Anvil (1518) is similar to anvils (1318, 1418) described above except as otherwise described below. Like anvils (1318, 1418), anvil (1518) includes an elongate anvil body (1520) having a plurality of staple forming pockets (not shown) arranged along an underside thereof, a connection member (1530) secured to a distal end of anvil body (1520), and a tapered distal tip (1522) rotatably coupled to connection member (1530). Like anvil tips (1322, 1422), anvil tip (1522) is configured to swivel relative to connection member (1530) and anvil body (1520) about a rotational axis disposed within a plane that contains the longitudinal axis of anvil body (1520) and a longitudinal centerline of a corresponding end effector having lower jaw (16). In particular, anvil tip (1522) is configured to swivel about the rotational axis between a first discrete position in which anvil tip (1522) is angled relative to anvil body (1520) in a direction toward lower jaw (16), and a second discrete position in which anvil tip (1522) extends distally straight from anvil body (1520) so as to be oriented away from lower jaw (16). Connection member (1530) and anvil tip (1522) define an angled interface (1432) therebetween that provides for the angular reorientation of anvil tip (1522) relative to the longitudinal axis of anvil body (1520) during rotation of anvil tip (1522) between the first and second discrete positions.

Anvil (1518) of the present example further includes a tip locking mechanism disposed at angled interface (1532) and configured to releasably retain anvil tip (1522) in each of the first and second discrete positions relative to anvil body (1520). As shown best in the disassembled view of FIG. 27, the present tip locking mechanism is shown in the form of an annular wave projection (1540) disposed at the base of shaft (1524) on an angled proximal face (1526) of anvil tip (1522); and a corresponding annular wave recess (1542) formed at the opening of bore (1534) on an angled distal face (1536) of connection member (1530). Though not shown, shaft (1524) may be retained axially within bore (1534) by a retention feature similar to rounded protrusion (1326) described above.

Axially raised portions of annular wave projection (1540) are configured to be received by corresponding axially recessed portions of annular wave recess (1542), and vice versa, when anvil tip (1522) is rotatably oriented in either the angled position shown in FIG. 27A or a straight position similar to that shown in FIG. 24. In any intermediate positions therebetween, raised portions of annular wave projection (1540) and of annular wave recess (1542) engage and drive axially against one another, thereby creating tension in shaft (1524). This resulting tension in shaft (1524) urges anvil tip (1522) rotationally toward the nearest straight or angled position, thus defining these positions as discrete positions.

Figure 28A:
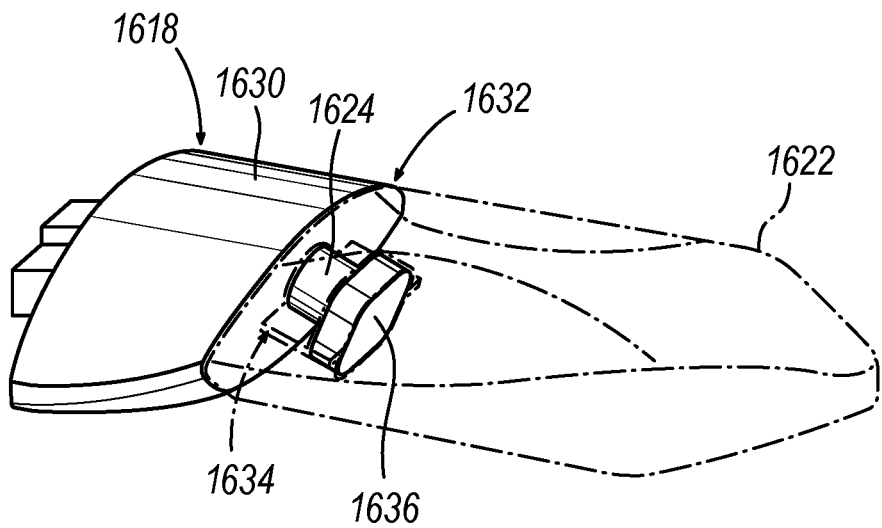
FIG. 28A depicts a perspective view of a distal portion of another exemplary anvil having a selectively rotatable distal and a tip locking mechanism, showing the distal tip in a second discrete position and in phantom to reveal features of the tip locking mechanism.
Figure 28B:
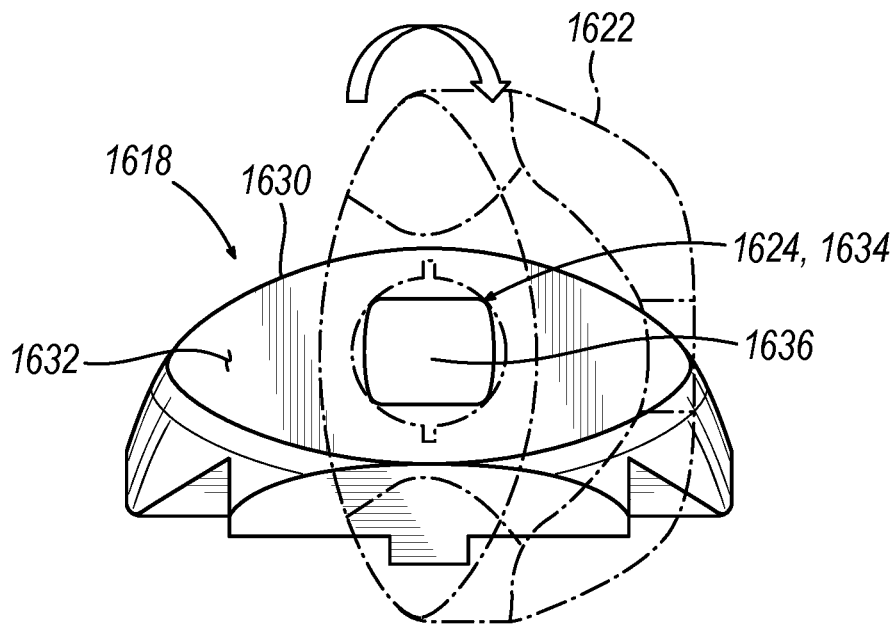
FIG. 28B depicts an end view of the distal portion of the anvil of FIG. 28A, showing the distal tip rotating relative to a connection member between the second discrete position and a first discrete position.

5. Anvil with Swiveling Tip Having Tip Locking Mechanism with Rotational Interference Feature FIGS. 28A-28B show a distal portion of another exemplary anvil (1618) suitable for use with any of the exemplary end effectors described above. Anvil (1618) is similar to anvils (1318, 1418, 1518) described above except as otherwise described below. Like anvils (1318, 1418, 1518), anvil (1618) includes an elongate anvil body (not shown) having a plurality of staple forming pockets arranged along an underside thereof, a connection member (1630) secured to a distal end of the anvil body, and a tapered distal tip (1622) rotatably coupled to connection member (1630). Like anvil tips (1322, 1422, 1522), anvil tip (1622) is configured to swivel relative to connection member (1630) about a rotational axis disposed within a plane that contains the longitudinal axis of the anvil body and a longitudinal centerline of a corresponding end effector having lower jaw (16). In particular, anvil tip (1622) is configured to swivel about the rotational axis between a first discrete position in which anvil tip (1622) is angled relative to the anvil body in a direction toward lower jaw (16), and a second discrete position in which anvil tip (1622) extends distally straight from the anvil body so as to be oriented away from lower jaw (16). Connection member (1630) and anvil tip (1622) define an angled interface (1632) therebetween that provides for the angular reorientation of anvil tip (1622) relative to the longitudinal axis of the anvil body during rotation of anvil tip (1622) between the first and second discrete positions.

In the present version, connection member (1630) includes a shaft (1634) that extends distally from an angled distal face thereof and is rotatably received within a corresponding bore (1624) formed within anvil tip (1622). Shaft (1634) and bore (1624) thus cooperate to define the axis about which anvil tip (1622) rotates relative to connection member (1630) between the first and second discrete positions. As shown best in FIG. 28A, shaft (1634) includes a cylindrical proximal portion and a distal cap (1636) having a non-circular cross-sectional shape. Shaft (1634) and bore (1624) also cooperate to define a tip locking mechanism configured to releasably retain anvil tip (1522) in each of the first and second discrete positions relative to connection member (1630). In particular, shaft cap (1636) and bore (1624) are suitably shaped to contact one another with an interference engagement when anvil tip (1622) is rotated between the angular and straight positions. This interference engagement results in resilient deflection of shaft cap (1636) and/or anvil tip (1622), which urges anvil tip (1622) toward the nearest straight or angled position.

6. Anvil with Swiveling Tip and Independent Captured Shaft

FIG. 29 shows a distal portion of another exemplary anvil (1718) suitable for use with any of the exemplary end effectors described above. Anvil (1718) is similar to anvils (1318, 1418, 1518, 1618) described above except as otherwise described below. Like anvils (1318, 1418, 1518, 1618), anvil (1718) includes an elongate anvil body (not shown) having a plurality of staple forming pockets arranged along an underside thereof, a connection member (1730) secured to a distal end of the anvil body, and a tapered distal tip (1722) rotatably coupled to connection member (1730). Like anvil tips (1322, 1422, 1522, 1622), anvil tip (1722) is configured to swivel relative to connection member (1730) about a rotational axis disposed within a plane that contains the longitudinal axis of the anvil body and a longitudinal centerline of a corresponding end effector having lower jaw (16). In particular, anvil tip (1722) is configured to swivel about the rotational axis between a first discrete position in which anvil tip (1722) is angled relative to the anvil body in a direction toward lower jaw (16), and a second discrete position in which anvil tip (1722) extends distally straight from the anvil body so as to be oriented away from lower jaw (16). Connection member (1730) and anvil tip (1722) define an angled interface (1732) therebetween that provides for the angular reorientation of anvil tip (1722) relative to the longitudinal axis of the anvil body during rotation of anvil tip (1722) between the first and second discrete positions.

As shown in FIG. 29, connection member includes a first bore (1734) that extends obliquely to a longitudinal axis of connection member (1730) and the anvil body, and anvil tip (1722) includes a second bore (1736) that aligns coaxially with first bore (1734). A shaft (1740) provided independently of anvil tip (1722) and connection member (1730) is disposed within first and second bores (1734, 1736) and enables anvil tip (1722) to rotate relative to connection member (1730) between the first and second discreet positions. As shown in FIG. 30, a proximal end of shaft (1740) includes a radially enlarged head (1742), and a distal end of shaft (1740) includes an annular groove (1744). Shaft (1740) is configured to be received within first and second bores (1734, 1736) such that proximal head (1742) seats against an internal stop shoulder (not shown) of first bore (1734), and such that annular groove (1744) is exposed through a distal end of second bore (1736) so that a C-clip (1746) can be applied to annular groove (1744). The proximal portion of shaft (1740) may be received by first bore (1734) with a press-fit engagement while the distal portion of shaft (1740) is received within second bore (1736) with a slip-fit engagement, thus permitting rotation of anvil tip (1722) about anvil shaft (1740) while anvil tip (1722) is retained axially on shaft (1740) by C-clip (1746).

Anvil (1718) may further include a tip locking mechanism operable to releasably retain anvil tip (1722) in the first and second discrete positions relative to connection member (1730) and the anvil body. In the present version, a detent recess (1748) is provided on the distal portion of shaft (1740) in annular groove (1744) and is configured to engage a corresponding detent protrusion (not shown) secured to anvil tip (1722). In other versions, a reverse configuration may be provided in which shaft (1740) is fixed to anvil tip (1722) and is rotatably disposed within first bore (1734) of connection member (1730), where the proximal portion of shaft (1740) provides a first detent feature and connection member (1730) provides a second detent feature. Furthermore, it will be appreciated that various other types of tip locking mechanisms may be employed.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler, comprising: (a) a body; (b) a shaft extending from the body, wherein the shaft defines a longitudinal axis; and (c) an end effector in communication with the shaft, wherein the end effector is operable to compress, staple, and cut tissue, wherein the end effector comprises: (i) a first jaw; (ii) a second jaw opposed from the first jaw, wherein the first and second jaws are operable to transition from an open state to a closed state to clamp tissue therebetween; and (iii) a tip member coupled with a distal end of the first jaw, wherein the tip member is selectively rotatable along a rotation axis to toggle between a first discrete position and a second discrete position, wherein the tip member in the first discrete position is configured to assume a first orientation relative to the second jaw, and the tip member in the second discrete position is configured to assume a second orientation relative to the second jaw.

Example 2

The surgical stapler of Example 1, wherein the tip member is configured to maintain either the first discrete position or the second discrete position unless acted upon by an external force.

Example 3

The surgical stapler of any one or more of Example 1 through Example 2, wherein the first jaw extends distally along a first jaw axis, wherein the tip member is rotatable between the first and second discrete positions about a rotational axis that extends within a plane that contains the first jaw axis.

Example 4

The surgical stapler of any one or more of Example 1 through Example 3, wherein the tip member is configured to rotate 180 degrees relative to the first jaw between the first and second discrete positions.

Example 5

The surgical stapler of any one or more of Example 1 through Example 4, wherein when the first and second jaws are in the closed state, the tip member in the first discrete position is configured to be obliquely oriented relative to the second jaw, and the tip member in the second discrete position is configured to be parallel to the second jaw.

Example 6

The surgical stapler of any one or more of Example 1 through Example 5, wherein a proximal end of the tip member defines a first angled face configured to abut a second angled face disposed proximal to the tip member, wherein the first and second angled faces are configured to engage one another in a first configuration to provide the tip member in the first discrete position, wherein the first and second angled faces are configured to engage one another in a second configuration to provide the tip member in the second discrete position.

Example 7

The surgical stapler of Example 6, wherein angles of the first and second angled faces are summated when the tip member is in the first discrete position to orient a longitudinal axis of the tip member obliquely relative to a longitudinal axis of the first jaw, wherein the angles of the first and second angled faces are negated when the tip member is in the second discrete position Example 8

The surgical stapler of any one or more of Example 6 through Example 7, wherein in the second discrete position the longitudinal axis of the tip member extends parallel to the longitudinal axis of the first jaw.

Example 9

The surgical stapler of any one or more of Example 1 through Example 8, further comprising a locking mechanism configured to releasably retain the tip member relative to the first jaw in each of the first and second discrete positions.

Example 10

The surgical stapler of Example 9, wherein the locking mechanism comprises a first detent feature provided by the tip member and a second detent feature disposed proximal to the tip member.

Example 11

The surgical stapler of any one or more of Example 1 through Example 10, further comprising a connection member that couples the tip member with the distal end of the first jaw.

Example 12

The surgical stapler of Example 11, wherein one of the connection member or the tip member includes a bore, wherein the surgical instrument end effector further comprises a shaft rotatably disposed within the bore and configured to enable rotation of the tip member relative to the first jaw between the first and second discrete positions.

Example 13

The surgical stapler of any one or more of Example 11 through Example 12, wherein a proximal end of the tip member defines a first angled face, wherein a distal end of the connection member defines a second angled face configured to engage the first angled face in each of the first and second discrete positions of the tip member.

Example 14

The surgical stapler of any one or more of Example 11 through Example 13, wherein the connection member includes a first locking feature, wherein the tip member includes a second locking feature configured to engage the first locking feature to releasably retain the tip member in each of the first and second discrete positions.

Example 15

The surgical stapler of any one or more of Example 1 through Example 14, wherein the tip member is rotatable relative to the first jaw between the first and second discrete positions about an axis that extends transversely to a longitudinal axis of the first jaw.

Example 16

A surgical stapler, comprising: (a) a body; (b) a shaft extending from the body, wherein the shaft defines a longitudinal axis; and (c) an end effector in communication with the shaft, wherein the end effector is operable to compress, staple, and cut tissue, wherein the end effector comprises: (i)

a first jaw configured to retain a cartridge configured to hold one or more staples, wherein the first jaw extends distally along a first jaw axis, (ii) a second jaw comprising an anvil, wherein the first and second jaws are operable to transition between an open state and a closed state, and (iii) a tip member coupled with a distal end of the first jaw, wherein the tip member is selectively rotatable relative to the first jaw between first and second discrete positions about a rotational axis that extends within a plane that contains the first jaw axis.

Example 17

The surgical stapler of Example 16, wherein the tip member in the first discrete position is configured to assume a first orientation relative to the second jaw, and wherein the tip member in the second discrete position is configured to assume a second orientation relative to the second jaw.

Example 18

The surgical stapler of any one or more of Example 16 through Example 17, wherein the tip member is configured to be rotated 180 degrees between the first and second discrete positions.

Example 19

An anvil configured for use with an end effector of a surgical stapler, wherein the anvil comprises: (a) a body defining a longitudinal body axis; (b) a plurality of staple forming pockets arranged along a length of the body; and (c) a tip member coupled with a distal end of the body and having a longitudinal tip axis, wherein the tip member is rotatable relative to the body about a rotational axis that extends within a plane that contains the longitudinal body axis, wherein the tip member is selectively rotatable relative to the body about the rotational axis between a first discrete position in which the longitudinal tip axis is in a first orientation relative to the longitudinal body axis, and a second discrete position in which the longitudinal tip axis is in a second orientation relative to the longitudinal body axis.

Example 20

The anvil of Example 19, wherein the rotational axis intersects the longitudinal body axis.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 16/729,559, entitled "Surgical Stapler with Deflectable Distal Tip," filed on Dec. 30, 2019, now U.S. Pub. No. 2020/0237370 published on Jul. 30, 2020; and/or U.S. patent application Ser. No. 16/729,553, entitled "Surgical Stapler with Toggling Distal Tip," filed on Dec. 30, 2019, now U.S. Pub. No. 2020/0237368 published on Jul. 30, 2020. The disclosure of each of these U.S. patent applications is incorporated by reference herein.

It should also be understood that the teachings herein may be readily combined with various teachings in U.S. Pat. No. D836,198, entitled "Surgical Stapler End Effector with Varying Deck Height and Tissue Gripping Features," issued Dec. 18, 2018; U.S. Pat. No. D833,010, entitled "Circular Surgical Stapler End Effector with Varying Deck Height and Tissue Gripping Features," issued Nov. 6, 2018; U.S. Pat. Pub. No. 2018/0235610, entitled "Surgical Stapler with Insertable Distal Anvil Tip," published Aug. 23, 2018, issued as U.S. Pat. No. 10,729,434 on Aug. 4, 2020; U.S. Pat. Pub. No. 2018/0235611, entitled "Surgical Stapler with Cooperating Distal Tip Features on Anvil and Staple Cartridge," published Aug. 23, 2018, issued as U.S. Pat. No. 10,806,451 on Oct. 20, 2020; U.S. Pat. No. D836,199, entitled "Surgical Stapler with Bent Anvil Tip and Angled Staple Cartridge Tip," issued Dec. 18, 2018; U.S. Pat. Pub. No. 2018/0235619, entitled "Surgical Stapler with Bent Anvil Tip, Angled Staple Cartridge Tip, and Tissue Gripping Features," published Aug. 23, 2018, issued as U.S. Pat. No. 10,758,231 on Sep. 1, 2020; U.S. Pat. Pub. No. 2019/0000481, entitled "Method of Surgical Stapling with End Effector Component Having a Curved Tip," published Jan. 3, 2019; U.S. patent application Ser. No. 16/235,617, entitled "Method of Applying Buttresses to Surgically Cut and Stapled Sites," filed Dec. 28, 2018; , issued as U.S. Pat. No. 11,033,269 on Jun. 15, 2021; U.S. patent application Ser. No. 16/035,872, entitled "Permanent Attachment Means for Curved Tip of Component of Surgical Stapling Instrument," filed Jul. 16, 2018, issued as U.S. Pat. No. 10,973,515 on Apr. 13, 2021; U.S. patent application Ser. No. 16/035,803, entitled "Surgical Stapling End Effector Component with Deformable Tip Having Void," filed Jul. 16, 2018, issued as U.S. Pat. No. 10,786,252 on Sep. 29, 2020; U.S. patent application Ser. No. 16/035,821, entitled "Surgical Stapling End Effector Component with Deformable Tip Skewing in Multiple Planes," filed Jul. 16, 2018, issued as U.S. Pat. No. 11,179,154 on Nov. 23, 2021; U.S. patent application Ser. No. 16/035,825, entitled "Surgical Stapling End Effector Component with Articulation and Asymmetric Deformable Tip," filed Jul. 16, 2018, issued as U.S. Pat. No. 11,160,550 on Nov. 2, 2021; U.S. patent application Ser. No. 16/035,831, entitled "Permanent Attachment Means for Curved Tip of Component of Surgical Stapling Instrument," filed Jul. 16, 2018, issued as U.S. Pat. No. 10,912,558 on Feb. 9, 2021; U.S. patent application Ser. No. 16/035,834, entitled "Buttress Applier Cartridge for Surgical Stapler Having End Effector with Deflectable Curved Tip," filed Jul. 16, 2018, issued as U.S. Pat. No. 10,912,561 on Feb. 9, 2021. Various suitable ways in which the teachings herein may be combined with the teachings of the above U.S. patents, U.S. Patent Publications, and U.S. patent applications will be apparent to those of ordinary skill in the art. The disclosure of each of the above-cited U.S. Patents, U.S. patent Publications, and U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler, comprising:
   (a) a body;
   (b) a shaft extending from the body, wherein the shaft defines a longitudinal axis; and
   (c) an end effector in communication with the shaft, wherein the end effector is operable to compress, staple, and cut tissue, wherein the end effector comprises:
      (i) a first jaw that extends distally along a first jaw axis;
      (ii) a second jaw opposed from the first jaw, wherein the first and second jaws are operable to transition from an open state to a closed state to clamp tissue therebetween; and
      (iii) a tip member operatively coupled with a distal end of the first jaw, wherein the tip member extends longitudinally along a longitudinal tip axis, wherein the tip member is rotatable relative to the first jaw about a rotational axis that extends within a plane that contains the first jaw axis and the longitudinal tip axis, wherein the tip member is selectively rotatable relative to the first jaw about the rotational axis between a first discrete position in which the longitudinal tip axis is in a first orientation relative to the first jaw axis, and a second discrete position in which the longitudinal tip axis is in a second orientation relative to the first jaw axis.

2. The surgical stapler of claim 1, wherein the tip member is configured to maintain either the first discrete position or the second discrete position unless acted upon by an external force.

3. The surgical stapler of claim 1, wherein the second jaw extends distally along a second jaw axis, wherein the tip member is rotatable between the first and second discrete positions about the rotational axis that extends within a plane that contains the first jaw axis and the second jaw axis.

4. The surgical stapler of claim 1, wherein the tip member is configured to rotate 180 degrees relative to the first jaw between the first and second discrete positions.

5. The surgical stapler of claim 1, wherein when the first and second jaws are in the closed state, the tip member in the first discrete position is configured to be obliquely oriented relative to the second jaw, and the tip member in the second discrete position is configured to be parallel to the second jaw.

6. The surgical stapler of claim 1, wherein a proximal end of the tip member defines a first angled face configured to abut a second angled face disposed proximal to the tip member, wherein the first and second angled faces are configured to engage one another in a first configuration to provide the tip member in the first discrete position, wherein the first and second angled faces are configured to engage one another in a second configuration to provide the tip member in the second discrete position.

7. The surgical stapler of claim 6, wherein angles of the first and second angled faces are summated when the tip member is in the first discrete position to orient the longitudinal tip axis obliquely relative to the first jaw, wherein the angles of the first and second angled faces are negated when the tip member is in the second discrete position.

8. The surgical stapler of claim 6, wherein in the second discrete position the longitudinal tip axis of the tip member extends parallel to the longitudinal axis of the first jaw.

9. The surgical stapler of claim 1, further comprising a locking mechanism configured to releasably retain the tip member relative to the first jaw in each of the first and second discrete positions.

10. The surgical stapler of claim 9, wherein the locking mechanism comprises a first detent feature provided by the tip member and a second detent feature disposed proximal to the tip member.

11. The surgical stapler of claim 1, further comprising a connection member that couples the tip member with the distal end of the first jaw.

12. The surgical stapler of claim 11, wherein one of the connection member or the tip member includes a bore, wherein the end effector further comprises a shaft rotatably disposed within the bore and configured to enable rotation of the tip member relative to the first jaw between the first and second discrete positions.

13. The surgical stapler of claim 11, wherein a proximal end of the tip member defines a first angled face, wherein a distal end of the connection member defines a second angled face configured to engage the first angled face in each of the first and second discrete positions of the tip member.

14. The surgical stapler of claim 11, wherein the connection member includes a first locking feature, wherein the tip member includes a second locking feature configured to engage the first locking feature to releasably retain the tip member in each of the first and second discrete positions.

15. A surgical stapler, comprising:
(a) a body;
(b) a shaft extending from the body, wherein the shaft defines a longitudinal axis; and
(c) an end effector in communication with the shaft, wherein the end effector is operable to compress, staple, and cut tissue, wherein the end effector comprises:
(i) a first jaw comprising an anvil, wherein the first jaw extends distally along a first jaw axis,
(ii) a second jaw extending distally along a second jaw axis, wherein the second jaw is configured to retain a stapling assembly that includes one or more staples, wherein the first and second jaws are operable to transition between an open state and a closed state, and
(iii) a tip member coupled with a distal end of the first jaw, wherein the tip member is selectively rotatable relative to the first jaw between first and second discrete positions about a rotational axis that extends within a plane that contains the first jaw axis and the second jaw axis, wherein the rotational axis extends at an oblique angle relative to the first jaw axis.

16. The surgical stapler of claim 15, wherein the tip member in the first discrete position is configured to assume a first orientation relative to the second jaw, and wherein the tip member in the second discrete position is configured to assume a second orientation relative to the second jaw.

17. The surgical stapler of claim 16, wherein the tip member is configured to be rotated 180 degrees between the first and second discrete positions.

18. The surgical stapler of claim 15, wherein the tip member extends longitudinally along a longitudinal tip axis, wherein the tip member is selectively rotatable relative to the anvil about the rotational axis between the first discrete position in which the longitudinal tip axis is in the first orientation relative to the first jaw axis, and the second discrete position in which the longitudinal tip axis is in a second orientation relative to the first jaw axis.

19. An anvil configured for use with an end effector of a surgical stapler, wherein the anvil comprises:
(a) a body extending longitudinally along a longitudinal body axis;
(b) a plurality of staple forming pockets arranged along a length of the body; and
(c) a tip member coupled with a distal end of the body and extending longitudinally along a longitudinal tip axis, wherein the tip member is rotatable relative to the body about a rotational axis that extends within a plane that contains the longitudinal body axis and the longitudinal tip axis, wherein the tip member is selectively rotatable relative to the body about the rotational axis between a first discrete position in which the longitudinal tip axis is in a first orientation relative to the longitudinal body axis, and a second discrete position in which the longitudinal tip axis is in a second orientation relative to the longitudinal body axis.

20. The anvil of claim 19, wherein the rotational axis intersects the longitudinal body axis.

* * * * *